(12) United States Patent
Hay et al.

(10) Patent No.: US 6,696,418 B1
(45) Date of Patent: *Feb. 24, 2004

(54) SOMATOSTATIN ANTAGONISTS AND AGONISTS THAT ACT AT THE SST SUBTYPE 2 RECEPTOR

(75) Inventors: Bruce A. Hay, East Lyme, CT (US); Anthony P. Ricketts, Stonington, CT (US); Bridget M. Cole, Stonington, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/618,029

(22) Filed: Jul. 17, 2000

Related U.S. Application Data

(60) Provisional application No. 60/151,830, filed on Sep. 1, 1999.

(51) Int. Cl.$^7$ ................................................. C07K 5/06
(52) U.S. Cl. ........................... 514/19; 544/358; 546/26
(58) Field of Search ........................... 514/19; 544/358; 546/26

(56) References Cited

U.S. PATENT DOCUMENTS 5,936,089 A    8/1999   Carpino et al. ............. 546/143

FOREIGN PATENT DOCUMENTS

| WO | WO98/44921 | 10/1998 |
| WO | 98/44922 | * 10/1998 |
| WO | WO98/45285 | 10/1998 |
| WO | WO 99/22735 | 5/1999 |
| WO | WO99/64401 | 12/1999 |
| WO | WO99/64420 | 12/1999 |

OTHER PUBLICATIONS

Bruce A. Hay, et al., "Small Molecule Somatostatin Receptor Subtype–2 Antagaonists", Biorganic & Medicinal Chemistry Letters 11 (2001) pp. 2731–2734.

L. Yang, et al. "Spiro[1H–indene–1,4–piperidine] Derivatives as Potent and Selective Non–Peptide Human Somatostatin Receptor Subtype 2 (SST2) Agonists", Journal of Medicinal Chemistry, vol. 41, No. 13, pp. 2175–2179 (1998).

Sadaf Farooqu et al., "The Therapeutic Value of Somastatin and its Analogues" Pituitary vol. 2, pp. 79–88 (1999).

Susan P. Rohrer, et al., "Rapid Identification of Subtype–Selective Agonists of the Somatostatin Receptor Through Combinatorial Chemistry" Science vol. 282, pp. 737–740; (1998).

Henning Grønbæk, et al. "Potential Role of Octreotide in the Treatment of Diabetes" Prog Basic Clin Pharmacol. Basel, vol. 10, pp. 103–128; (1996).

Vicente Martinez, et al., "High Basal Gastric Acid Secreations in Somatostatin Receptor Subtype 2 Knockout Mice"; American Gastroenterology (1998) 114 pp. 1125–1132.

Yogesh C. Patel, et al., "Somatostatin Receptors", TEM, vol. 8, No. 10, (1997) pp. 398–404.

Lihu Yang, et al., "Synthesis and biological activities of potent peptidomimetics selective for somastostatin receptor subtype 2"; Proc. Natl. Acad. Sci. USA, vol. 95, pp. 10836–10841, (1998).

Simon J. Hocart, et al., "Potent Antagonists of Somatostatin: Synthesis and Biology"; J. Med. Chem. vol. 41, pp. 1146–1154.

Muhammad Zaki, et al., "Somatostatin Receptor Subtype 2 Mediates Inhibition of Gastrin and Histamine Secretion from Human, Dog and Rat Antrum"; Gastroenterology vol. 111, pp. 919–924 (1996).

William R. Baumbach, et al., "A Linear Hexpeptide Somatostatin Antagonists Blocks Somatostatin Activity In Vitro and Influences Growth Hormone Release in Rats" Molecular Pharmacology, vol. 54, pp. 864–873 (1998).

* cited by examiner

Primary Examiner—Christopher S. F. Low
Assistant Examiner—David Lukton
(74) Attorney, Agent, or Firm—Peter C. Richardson; Gregg C. Benson; E. Victor Donahue

(57) ABSTRACT

Compounds according to the formula:

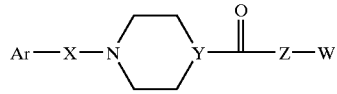

and pharmaceutically acceptable salts, solvates or hydrates thereof; wherein group Ar is optionally substituted ($C_6$–$C_{10}$) aryl or ($C_1$–$C_9$)heteroaryl; X is a direct link, —$CH_2$—, —$SO_2$—, —CO—, —$CHR^1$— where $R^1$ is ($C_1$–$C_6$) alkyl, or —$CR^1R^{1''}$— where both $R^{1'}$ and $R^{1''}$ are, independently, ($C_1$–$C_6$)alkyl; Y is N or CH; and Z and W are as herein defined, and pharmaceutical compositions thereof, and methods useful to facilitate secretion of growth hormone (GH) in mammals.

23 Claims, No Drawings

SOMATOSTATIN ANTAGONISTS AND AGONISTS THAT ACT AT THE SST SUBTYPE 2 RECEPTOR

The present application claims priority under 35 USC section 119 to U.S. Provisional Application No. 60/151,830 filed Sep. 1, 1999.

FIELD OF THE INVENTION

The present invention provides pharmaceutically active compounds that facilitate secretion of growth hormone (GH) by the anterior pituitary. Growth hormone (also known as somatotropin) acts indirectly to promote skeletal growth in children by stimulating the production of insulin like growth factor-1 from the liver. Growth hormone also stimulates the differentiation of fat cells and chondrocytes (cells that secrete collagen and proteoglycans to form cartilage). In adults, growth hormone is involved in the proper maintenence of connective and muscle tissues.

Growth hormone deficiency may be congenital or acquired. Deficiency in children causes slow skeletal growth that, if not corrected, results in permanent short stature. In older adults, deficiency of growth hormone results in frailty. Additional adult symptoms of GH deficiency may include wrinkled skin and hypoglycemia.

For veterinary application, upregulation of growth hormone is useful to treat frailty in older animals, particularly companion animals. With respect to livestock, upregulation of growth hormone increases growth and performance, even in healthy animals with normal GH levels. Improvements in feed efficiency, milk yield, leanness, meat quality and fertility are of note.

Although direct administration of growth hormone may be effective in certain therapeutic applications, it is difficult in practice. Among other issues, since the half-life of growth hormone in the body is very short, direct administration leads to artificially increased levels in the concentration of circulating GH, which then rapidly drop off. Sustained release, such as by a mechanical pump, has not been optimally set to practice.

The concentration of growth hormone circulating in the body depends on the balance of numerous biochemical pathways, including opposing processes. Compared to the direct administration approach, shifting the balance of these pathways indirectly provides a safer, more reproducible method to affect GH secretion on a sustained basis. Under this approach, since the overall regulatory framework remains intact, secretion rates and circulatory concentrations for GH follow a relatively normal pattern, and adverse fluctuations in both secretion rate and circulating GH concentration are avoided. The present invention provides for therapeutic compounds, and their use, to indirectly elevate growth hormone secretion from the pituitary.

Reported Developments

Growth hormone is released from the anterior pituitary in response to stimulation by growth hormone releasing peptide (GHRP), and growth hormone releasing hormone (GHRH), of hypothalmic origin. However, release of growth hormone via these or other mechanisms is inhibited by somatostatin, and thus the process is closely regulated.

Somatostatin (SRIF) is a cyclic peptide hormome of 14 amino acids (there is also a 28 amino acid form) having numerous endocrine functions which, like many hormones, is cleaved from a larger precursor protein. Somatostatin inhibits the pituitary secretion of growth hormone, the pancreatic secretion of glucagon and insulin, and the secretion of gastrin from the gut. Somatostatin also acts as a neurotransmitter/neuromodulator (see S. J. Hocart et al., *J. Med. Chem.*,41, pp. 1146–1154, 1998 for a general discussion).

The biological effects of somatostatin are apparently all inhibitory in nature, and are elicited upon binding to the surface of a target cell. The receptor is an integral membrane protein (which spans the cell membrane), and is G-protein-coupled. G-protein coupled receptors represent a major class of cell surface receptors. It is believed that upon binding of somatostatin to the receptor, the receptor undergoes a conformational change facilitating its interaction with a G-protein at the cytoplasmic face of the receptor. This facilitates binding or release of GTP/GDP at the G protein, and leads to further activation and signalling events inside the cell. In particular, somatostatin binding at its own G-protein-coupled receptor is negatively coupled to adenylyl cyclase activity, which is necessary for the production of cylic AMP. Thus, these further signalling events directly oppose mechanisms (for example, as mediated by calcium ions or cyclic AMP) whereby GHRP and GHRH would otherwise trigger extracellular secretion of growth hormone from cytoplasmic storage granules. For a general review thereof, see *The Encyclopedia of Molecular Biology*, J. Kendrew, ed., Blackwell Science, Ltd. 1994, at page 387.

The effects of somatostatin on target cells are mediated by at least 5 classes of receptors (sst1–sst5). Although the receptors may have similar affinity for somatostatin, they are differentially expressed in different tissues, and so positioned, interact, directly or indirectly, with different intracellular signalling components. This tissue specificity of receptor expression accounts in large measure for the different effects of somatostatin in different target cell types. Somatostatin receptors are found, for example, in tissues of the anterior pituitary, other brain tissues, the pancreas, the lung, on lymphocytes, and on mucosa cells of the intestinal tract.

The sst2 type receptor is known to mediate inhibition of growth hormone secretion in the anterior pituitary. This receptor is also reported in 2 forms, proteins sst2A and sst2B, which result from differential splicing of the sst2 gene transcript (M. Vanetti, et al., FEBS Letters, 311, pp.290–294, 1992). The sst2 receptor is also known to mediate inhibition of gastrin and histamine secretion. Additionally, the sst2 receptor is known to mediate inhibition of glucagon release from pancreatic alpha cells.

Although numerous somatostatin agonists have been described (see for example, WO 98/44922, WO 98/45285, and WO 98/44921), the development of useful sst2-linked somatostatin antagonists has lagged behind. Recent reports of such compounds include W. R. Baumbach et al., *Molecular Pharmacology*, 54, pp. 864–873, 1998, and S. J. Hocart et al., *J. Med. Chem.*, 41, pp. 1146–1154, 1998. However, such compounds are short peptides, a class of molecules not often suited for successful use as pharmaceuticals because of their typically short half life in the body.

It would be advantageous to provide antagonists of somatostatin activity, effective at the sst2 type receptor, having superior properties as pharmaceuticals, including bioavailability, stability, and the like. The present invention provides a series of antagonist compounds that specifically interfere with the binding of somatostatin to the sst subtype 2 receptors of cells in the mammalian anterior pituitary, and which have additional valuable properties.

SUMMARY OF THE INVENTION

Accordingly, there are provided compounds according to the formula

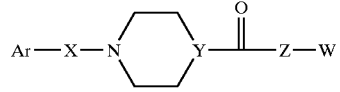

(formula I)

or pharmaceutically acceptable salts, solvates or hydrates thereof; wherein

Ar is $(C_6-C_{10})$aryl, or $(C_1-C_9)$heteroaryl;

X is a direct link, $-CH_2-$, $-SO_2-$, $-CO-$, $-CHR^1-$ where $R^1$ is $(C_1-C_6)$alkyl, or $-CR^{1'}R^{1''}-$ where both $R^{1'}$ and $R^{1''}$ are, independently, $(C_1-C_6)$alkyl;

Y is N or CH;

Z is selected from the groups consisting of:

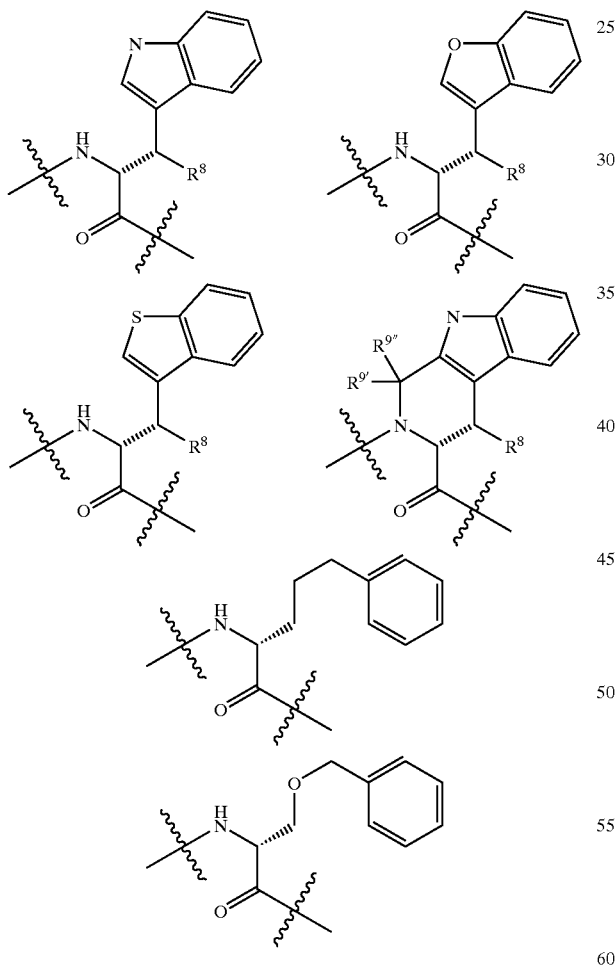

wherein $R^8$, if present, is H, or $(C_1-C_6)$ alkyl; and $R^{9'}$ and $R^{9''}$, if present, are each independently selected from the group consisting of H, $(C_1-C_6)$alkyl, $(C_1-C_9)$heteroaryl $(C_1-C_6)$alkyl, and $(C_6-C_{10})$aryl$(C_1-C_6)$alkyl;

W is selected from (a) and (b):

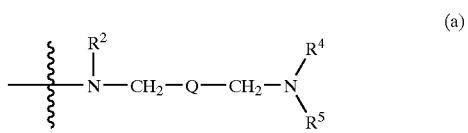

(a)

wherein $R^2$, $R^4$ and $R^5$ are each independently selected from: H; $(C_1-C_6)$alkyl, optionally substituted with one or more halo or trifluoromethyl groups; and benzyl, optionally substituted with one or more halo or trifluoromethyl groups; and Q is selected from
(i) $(C_6-C_{10})$ aryl,
(ii) $(C_1-C_9)$ heteroaryl,
(iii) $(C_3-C_{10})$cycloalkyl, and
(iv) $(C_3-C_{10})$heterocycloalkyl,
wherein each of said groups (i) to (iv) is optionally substituted with one or more groups that are independently selected from halo, $(C_1-C_4)$ alkoxy, and $(C_1-C_6)$ alkyl;

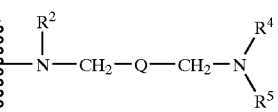

(b)

wherein $R^{2'}$, $R^{4'}$ and $R^{5'}$ are each independently selected from the group consisting of H; $(C_1-C_6)$ alkyl, optionally substituted by one or more halo or trifluoromethyl groups; and benzyl, also optionally substituted by one or more halo or trifluoromethyl groups;

n is 2 to 5; and $R^3$ is selected from the groups consisting of
(i) H; $(C_1-C_6)$ alkyl, optionally substituted by one or more halo or trifluoromethyl groups; and benzyl, also optionally substituted by one or more halo or trifluoromethyl groups;

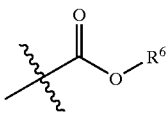

(ii)

n is 2 to 5; and $R^3$ is selected from the groups consisting of
(i) H; $(C_1-C_6)$ alkyl, optionally substituted by one or more halo or trifluoromethyl groups; and benzyl, also optionally substituted by one or more halo or trifluoromethyl groups;

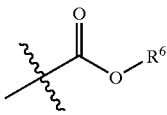

(ii)

where $R^6$ is H; $(C_1-C_6)$ alkyl, optionally substituted by one or more halo or trifluoromethyl groups; or benzyl, optionally substituted by one or more halo or trifluoromethyl groups; and

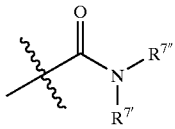

(iii)

where $R^{7'}$ and $R^{7''}$ are each, independently, H; $(C_1-C_6)$ alkyl, optionally substituted by one or more halo or trifluoromethyl groups; or benzyl, optionally substituted by one or more halo or trifluoromethyl groups.

Preferred compounds of the invention include those according to the formula

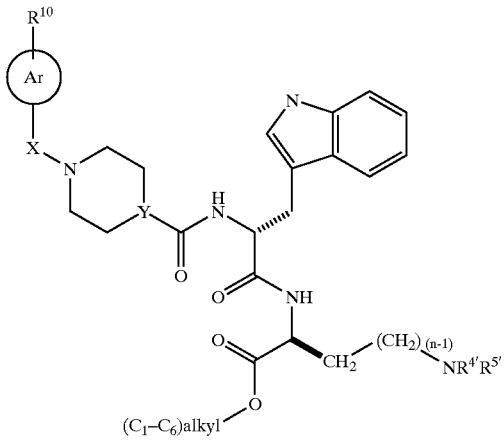

or pharmaceutically acceptable salts, solvates or hydrates thereof; wherein group Ar is a $(C_6-C_{10})$aryl or $(C_1-C_9)$heteroaryl group, as previously defined;

$R^{10}$ represents from 0 to 5 optional substituent groups, each independently selected from hydroxy, halo, amino, trifluoromethyl, carboxy, $(C_1-C_6)$alkoxy-, $(C_1-C_6)$acyloxy-, $(C_1-C_6)$alkylamino-, $((C_1-C_6)$alkyl$)_2$ amino-, $(C_1-C_6)$acylamino-, cyano, nitro, $(C_1-C_6)$alkyl-, $(C_2-C_6)$alkenyl-, $(C_2-C_6)$alkynyl-, $(C_1-C_6)$acylamino-, cyano$(C_1-C_6)$alkyl-, trifluoromethyl$(C_1-C_6)$alkyl-, nitro$(C_1-C_6)$alkyl-, $(C_1-C_3)$alkyl(difluoromethylene)$(C_1-C_3)$alkyl-, $(C_1-C_6)$acylamino$(C_1-C_6)$alkyl(difluoromethylene)-, $(C_1-C_3)$alkyl(difluoromethylene)$(C_1-C_3)$alkyl-, $(C_1-C_6)$alkoxy$(C_1-C_6)$acyl-, $(C_1-C_6)$alkylamino $(C_1-C_6)$acyl-, $(C_6-C_{10})$alkyl$)_2$amino$(C_1-C_6)$acyl-, $(C_6-C_{10})$aryl-, $C_5-C_9)$heteroaryl-, $(C_6-C_{10})$aryl $(C_1-C_6)$alkyl-, $(C_2-C_9)$heteroaryl$(C_1-C_6)$alkyl-, $(C_6-C_{10})$aryl$(C_6-C_{10})$aryl-, $(C_6-C_{10})$aryl$(C_6-C_{10})$aryl $(C_1-C_6)$alkyl- $(C_3-C_{10})$cycloalkyl-, $(C_3-C_6)$cycloalkyl $(C_1-C_6)$alky-, $(C_3-C_{10})$heterocycloalkyl-, $(C_3-C_{10})$ heterocycloalkyl$(C_1-C_6)$alkyl-, hydroxy$(C_2-C_6)$alkyl-, $(C_1-C_6)$acyloxy$(C_2-C_6)$alkyl-, $(C_1-C_6)$alkoxy$(C_2-C_6)$ alkyl-, piperazinyl$(C_1-C_6)$alkyl-, $(C_1-C_6)$acylamino $(C_1-C_6)$alkyl-, $(C_6-C_{10})$aryl$(C_1-C_6)$alkoxy$(C_1-C_6)$ alkyl-, $(C_2-C_9)$heteroaryl$(C_1-C_6)$alkoxy$(C_1-C_6)$alkyl-, $(C_1-C_6)$alkylthio$(C_1-C_6)$alkyl-, $(C_6-C_{10})$arylthio $(C_1-C_6)$alkyl-, $(C_1-C_6)$alkylsulfinyl$(C_1-C_6)$alkyl-, $(C_6-C_{10})$arylsulfinyl$(C_1-C_6)$alkyl-, $(C_1-C_6)$ alkylsulfonyl$(C_1-C_6)$alkyl, $(C_6-C_{10})$arylsulfonyl $(C_1-C_6)$alkyl-, amino$(C_1-C_6)$alkyl-, $(C_1-C_6)$ alkylamino$(C_1-C_6)$alkyl-, and $((C_1-C_6)$alkyl$)_2$amino $(C_1-C_6)$alkyl, wherein, preferably said $R^{10}$ is selected from halo, cyano, carboxy, $(C_1-C_6)$alkyl, and $(C_1-C_6)$ alkoxy, X is —$CH_2$—, —$SO_2$—, —CO—, or a direct link;
Y is CH or N;
(n-1) is 1 to 4; and $R^{4'}$ and $R^{5'}$ are each independently selected from H; $(C_1-C_6)$ alkyl, optionally substituted by one or more halo or trifluoromethyl groups; and benzyl, also optionally substituted by one or more halo or trifluoromethyl groups; wherein it is further preferred that $R^{4'}$ and $R^{5'}$ are each independently selected from hydrogen and methyl.

Additional preferred compounds include those according to the immediately preceeding formula, wherein group Ar group is phenyl, and, as before, between 0 and 5 substituents $R^{10}$ are optionally present.

Further preferred compounds of the invention are defined according to the following formula

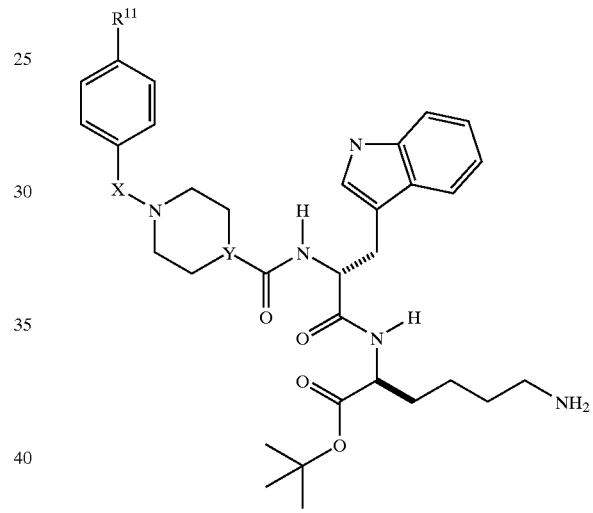

including the pharmaceutically acceptable salts, solvates, and hydrates thereof; wherein $R^{11}$ is selected as is $R^{10}$, and is preferably selected from halo, cyano, carboxy, $(C_1-C_6)$alkyl, and $(C_1-C_6)$ alkoxy;

X is —$CH_2$—, —$SO_2$—, —CO—, or a direct link; and
Y is CH or N.

Preferred compounds of the invention include:

6-Amino-2-[2-[(1-benzenesulfonyl-piperidine-4-carbonyl)-amino]-3-(1H-indol-3-yl)-propionylamino]-hexanoic acid tert-butyl ester;

6-Amino-2-[2-[(4-benzoyl-piperazine-1-carbonyl)-amino]-3-(1H-indol-3-yl)-propionylamino]-hexanoic acid tert-butyl ester;

6-Amino-2-(3-(1H-indol-3-yl)-2-{[4-(4-methyl-benzoyl)-piperazine-1-carbonyl]-amino}-propionylamino)-hexanoic acid tert-butyl ester;

6-Amino-2-[2-[(4-benzenesulfonyl-piperazine-1-carbonyl)-amino]-3-(1H-indol-3-yl)-propionylamino]-hexanoic acid tert-butyl ester; and 6-Amino-2-(3-(1H-indol-3-yl)-2-{[4-(toluene-4-sulfonyl)-piperazine-1-carbonyl]-amino}-propionylamino)-hexanoic acid tert-butyl ester.

Additional compounds of the invention include:

4-(Toluene-4-sulfonyl)-piperazine-1-carboxylic acid [1-[(4-aminomethyl-pyridin-2-ylmethyl)-carbamoyl]-2-(1H-indol-3-yl)-ethyl]-amide;
6-Amino-2-(3-(1H-indol-3-yl)-2-{[4-(toluene-4-sulfonyl)-piperazine-1-carbonyl]-amino}-butyrylamino)-hexanoic acid tert-butyl ester;
6-Amino-2-[2-{[4-(4-fluoro-benzenesulfonyl)-piperazine-1-carbonyl]-amino}-3-(1H-indol-3-yl)-propionylamino]-hexanoic acid tert-butyl ester;
4-Benzenesulfonyl-piperazine-1-carboxylic acid [1-[(4-aminomethyl-pyridin-2-ylmethyl)-carbamoyl]-2-(1H-indol-3-yl)-ethyl]-amide;
6-Amino-2-[2-[(4-benzenesulfonyl-piperazine-1-carbonyl)-amino]-3-(1H-indol-3-yl)-butyrylamino]-hexanoic acid tert-butyl ester;
6-Amino-2-[2-{[4-(4-chloro-benzenesulfonyl)-piperazine-1-carbonyl]-amino}-3-(1H-indol-3-yl)-propionylamino]-hexanoic acid tert-butyl ester;
4-(4-Methyl-benzoyl)-piperazine-1-carboxylic acid [1-[(4-aminomethyl-pyridin-2-ylmethyl)-carbamoyl]-2-(1H-indol-3-yl)-ethyl]-amide;
6-Amino-2-(3-(1H-indol-3-yl)-2-{[4-(4-methyl-benzoyl)-piperazine-1-carbonyl]-amino}-butyrylamino)-hexanoic acid tert-butyl ester;
6-Amino-2-[2-{[4-(4-fluoro-benzoyl)-piperazine-1-carbonyl]-amino}-3-(1H-indol-3-yl)-propionylamino]-hexanoic acid tert-butyl ester;
4-Benzoyl-piperazine-1-carboxylic acid [1-[(4-aminomethyl-pyridin-2-ylmethyl)-carbamoyl]-2-(1H-indol-3-yl)-ethyl]-amide;
6-Amino-2-[2-[(4-benzoyl-piperazine-1-carbonyl)-amino]-3-(1H-indol-3-yl)-butyrylamino]-hexanoic acid tert-butyl ester;
6-Amino-2-[2-{[4-(4-chloro-benzoyl)-piperazine-1-carbonyl]-amino}-3-(1H-indol-3-yl)-propionylamino]-hexanoic acid tert-butyl ester;
1-(Toluene-4-sulfonyl)-piperidine-4-carboxylic acid [1-[(4-aminomethyl-pyridin-2-ylmethyl)-carbamoyl]-2-(1H-indol-3-yl)-ethyl]-amide;
6-Amino-2-(3-(1H-indol-3-yl)-2-{[1-(toluene-4-sulfonyl)-piperidine-4-carbonyl]-amino}-butyrylamino)-hexanoic acid tert-butyl ester;
6-Amino-2-[2-{[1-(4-fluoro-benzenesulfonyl)-piperidine-4-carbonyl]-amino}-3-(1H-indol-3-yl)-propionylamino]-hexanoic acid tert-butyl ester;
1-Benzenesulfonyl-piperidine-4-carboxylic acid [1-[(4-aminomethyl-pyridin-2-ylmethyl)-carbamoyl]-2-(1H-indol-3-yl)-ethyl]-amide;
6-Amino-2-[2-[(1-benzenesulfonyl-piperidine-4-carbonyl)-amino]-3-(1H-indol-3-yl)-butyrylamino]-hexanoic acid tert-butyl ester;
6-Amino-2-[2-{[1-(4-chloro-benzenesulfonyl)-piperidine-4-carbonyl]-amino}-3-(1H-indol-3-yl)-propionylamino]-hexanoic acid tert-butyl ester;
1-(4-Methyl-benzoyl)-piperidine-4-carboxylic acid [1-[(4-aminomethyl-pyridin-2-ylmethyl)-carbamoyl]-2-(1H-indol-3-yl)-ethyl]-amide;
6-Amino-2-(3-(1H-indol-3-yl)-2-{[1-(4-methyl-benzoyl)-piperidine-4-carbonyl]-amino}-butyrylamino)-hexanoic acid tert-butyl ester;
6-Amino-2-[2-{[1-(4-fluoro-benzoyl)-piperidine-4-carbonyl]-amino}-3-(1H-indol-3-yl)-propionylamino]-hexanoic acid tert-butyl ester;
1-Benzoyl-piperidine-4-carboxylic acid [1-[(4-aminomethyl-pyridin-2-ylmethyl)-carbamoyl]-2-(1H-indol-3-yl)-ethyl]-amide;
6-Amino-2-[2-[(1-benzoyl-piperidine-4-carbonyl)-amino]-3-(1H-indol-3-yl)-butyrylamino]-hexanoic acid tert-butyl ester; and
6-Amino-2-[2-{[1-(4-chloro-benzoyl)-piperidine-4-carbonyl]-amino}-3-(1H-indol-3-yl)-propionylamino]-hexanoic acid tert-butyl ester.

The compound of formula (I) may have chiral centers and therefore exist in different enantiomeric forms. This invention relates to all optical isomers, tautomers and stereoisomers of the compounds of formula (I), and mixtures thereof, although as will be described below in greater detail, certain isomeric structures are preferred.

The present invention also relates to the pharmaceutically acceptable acid addition salts of compounds of the formula (I). The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

With respect to the relatively limited number of compounds that so permit, the invention also relates to base addition salts of formula (I). The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The subject invention also includes isotopically-labelled compounds, which are identical to those recited in Formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of Formula (I) of this invention and prodrugs thereof can generally be prepared by carrying out the procedures disclosed in the Schemes and/or in the Examples and Preparations below, by substituting a readily available isotopically labelled reagent for a non-isotopically labelled reagent.

The present invention also relates to a pharmaceutical composition for increasing growth hormone secretion in a mammal, including a human, comprising an effective amount of a compound according to formula 1, and a pharmaceutical carrier. The present invention also relates to a pharmaceutical composition for increasing gastrin secretion or glucagon secretion in a mammal, comprising an effective amount of a compound according to formula 1, and a pharmaceutical carrier.

The present invention also relates to a pharmaceutical composition for the treatment of diseases characterized by decreased levels of growth hormone, glucagon, or gastrin in a mammal, including a human, comprising an amount of a compound of formula (I) effective in such treatments and a pharmaceutically acceptable carrier. The present invention also relates to a pharmaceutical composition for the treatment of diseases in a mammal, including a human, wherein treatment can be effected by inhibiting the binding of somatostatin to the sst2-type receptor therefor, comprising an effective amount of a compound according to formula 1, and a pharmaceutical carrier.

The present invention relates to a method for treating growth hormone deficiency in a mammal, including a human. The present invention also relates to elevating the level of growth hormone in a mammal, including a human, wherein this is beneficial to the mammal nothwithstanding that the natural levels of growth hormone present in the mammal are within the normal range. In the practice of said method, there is administered a pharmaceutical composition of the invention comprising a compound according to formula (1), and a pharmceutical carrier.

Similarly, the methods of the invention provide for increasing gastrin secretion or glucagon secretion in a mammmal, including a human, where this is medically appropriate. For example, gastrin is involved in protection of gastric mucosa against damage by chemical substances, e.g. alcohol (S. J. Konturek et al., *European Journal of Pharmacology*, 278(3), pp. 203–212, 1995). Glucagon is a counter-regulatory hormone that is used to treat hypoglycemia, and causes positive inotropic and chronotropic effects without the need for beta-1 adrenoceptor stimulation. It also can be used to correct beta-blocker, verapamil and imipramine overdose, and is used as adjunctive therapy in shock situations, for heart failure, and in treating post-countershock asystole (see C. M. White, *Journal of Clinical Pharmacology,*. 39(5), pp. 442–447,1999)

In preferred examples of the invention, there are provided methods for treating a human for one or more symptoms of insufficient growth hormone secretion, or one or more conditions that may occur therewith and be exacerbated thereby, wherein said condition is selected from frailty, hypoglycemia, wrinkled skin, slow skeletal growth, reduced immune function, reduced organ function, fertility disorders, bone disease, AIDS-related complex, cachexia, cardiac failure, ischemic heart disease, colon disease, metabolic disorders, renal failure, muscular dystrophy, and Turners syndrome, comprising administering an effective amount of a pharmaceutical composition as aforementioned. It will be appreciated that numerous of the above conditions also affect non-human mammals, and treatment of such conditions is also within the practice of the invention.

In a further preferred example of the invention, there is provided a method for treating a non-human mammal to enhance the growth and performance thereof, comprising administering an effective amount of a pharmaceutical composition as aforementioned. Enhancement of growth and performance includes, for example, increased feed efficiency, improved milk yield or fertility, and increased leanness.

A highly preferred example of the invention provides a method whereinby secretion of growth hormone, gastrin, or glucagon can be increased on a sustained basis in a mammal, including a human, in need thereof, comprising adminstering a dose of a pharmaceutical composition as aforementioned. According to this example of the invention, physiologically adverse consequences of artificial fluctuations in the circulating (or locally needed) concentrations of these hormones can be avoided.

Although the pharmaceutical compositions and methods of the invention are described primarily in terms of use with humans, and non-human mammals, the skilled practitioner will immediately appreciate that the invention, in many of its aspects, may be usefully practiced with respect to birds, such as chickens and turkeys, and also fishes.

Definitions

In connection with the practice of the invention, the following definitions will generally apply.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "alkyl", as used herein, unless otherwise indicated, includes saturated monovalent hydrocarbon radicals having straight, branched or cyclic moieties or combinations thereof. Similarly, the terms "alkenyl" and "alknyl" define hydrocarbon radicals having straight, branched or cyclic moities wherein at least one double bond, or at least one triple bond, respectively, is present. Such definitions also apply when the alkyl, alkenyl or alkynyl group is present within another group, such as alkoxy or alkylamine.

The term "alkoxy", as used herein, includes O-alkyl groups wherein "alkyl" is as defined above.

The term "halo", as used herein, unless otherwise indicated, includes fluoro, chloro, bromo or iodo.

An "aryl" group as used herein, unless otherwise indicated, includes an organic radical derived from a monocyclic or bicyclic ($C_6$–$C_{10}$) aromatic hydrocarbon compound by removal of a hydrogen radical from a ring carbon of the aryl compound. An aryl group is optionally substituted by one or more substituents wherein, unless otherwise indicated, selection of each optional substituent is independent of selection of any other optional subsituents, and perferably the number of optional substituents is between 0 and 3, more preferably between 0 and 2. It will be appreciated that the preferred number of substituents is determined in part by facility of synthesis. Representative aryl groups are phenyl and naphthyl.

A "heteroaryl" group as used herein, unless otherwise indicated, includes an organic radical derived from a monocyclic or bicyclic ($C_1$–$C_9$) aromatic heterocyclic compound by removal of a hydrogen radical from a ring atom of the heteroaryl compound, said ring atom being uncharged in said compound. A heteroaryl group is optionally substituted by one or more substituents wherein, unless otherwise indicated, selection of each optional substituent is independent of selection of any other optional substituents, and perferably the number of optional substituents is between 0 and 3, more preferably between 0 and 2. It will be appreciated that the preferred number of substituents is determined in part by facility of synthesis. Representative heteroaryl groups include furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydroquinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, and benzoxazinyl; and the like.

A "cycloalkyl" group as used herein, unless otherwise indicated, includes an organic radical derived from a monocyclic ($C_3$–$C_{10}$)cycloalkyl compound, by removal of a hydrogen radical from a ring carbon of the cycloalkyl compound. A cycloalkyl group is optionally substituted by one or more substituents wherein, unless otherwise indicated, selection of each optional substituent is independent of selection of any other optional substituents, and perferably the number of optional substituents is between 0 and 3, more preferably between 0 and 2. It will be appreciated that the preferred number of substituents is determined in part by facility of synthesis. Representative cycloalkyl groups include cyclopropyl, cyclobutyl, cyclopentyl, cyclohexyl, cycloheptyl, cyclopropenyl, cyclobutenyl, cyclopentenyl, cyclohexenyl, cycloheptenyl, 1,3-cyclobutadienyl, 1,3-cyclopentadienyl, 1,3-cyclohexadienyl, 1,4-cyclohexadienyl, 1,3-cycloheptadienyl, 1,4-cycloheptadienyl, 1,3,5-cycloheptatrienyl, bicyclo[3.2.1]octane, bicyclo[2.2.1] heptane, and the norborn-2-ene unsaturated form thereof. Thus, the term cycloalkyl also includes cycloalkenyl groups having one or two double bonds.

A "heterocycloalkyl" group as used herein, unless otherwise indicated, includes an organic radical derived from a monocyclic ($C_3$–$C_{10}$)heterocycloalkyl compound by removal of a hydrogen radical from a ring atom of the heterocycloalkyl compound. A heterocycloalkyl group is optionally substituted by one or more substituents wherein, unless otherwise indicated, selection of each optional substituent is independent of selection of any other optional substituents, and perferably the number of optional substituents is between 0 and 3, more preferably between 0 and 2. It will be appreciated that the preferred number of substituents is determined in part by facility of synthesis. Representative heterocycloalkyl groups include pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, and chromanyl.

In connection with the terms "aryl" group, "heteroaryl" group, "cycloalkyl" group and "heterocycloalkyl" group, as herein defined, the term "optionally substituted" means that one or more chemically and pharmaceutically acceptable functional groups may be bonded thereto. Such a group contributes properties useful to production, storage, or use of the inventive compounds as pharmaceuticals, or at least does not substantially negate their pharmacological activity. Such suitable substituents may be determined by those skilled in the art. Illustrative examples of suitable substituents include, but are not limited to, hydroxy, halo, amino, trifluoromethyl, carboxy, ($C_1$–$C_6$)alkoxy-, ($C_1$–$C_6$)acyloxy-, ($C_1$–$C_6$)alkylamino-, (($C_1$–$C_6$)alkyl)$_2$amino-, ($C_1$–$C_6$)acylamino-, cyano, nitro, ($C_1$–$C_6$)alkyl-, ($C_2$–$C_6$)alkenyl-, ($C_2$–$C_6$)alkynyl-, ($C_1$–$C_6$)acylamino-, cyano($C_1$–$C_6$)alkyl-, trifluoromethyl($C_1$–$C_6$)alkyl-, nitro($C_1$–$C_6$)alkyl-, ($C_1$–$C_3$)alkyl(difluoromethylene)($C_1$–$C_3$)alkyl-, ($C_1$–$C_6$)acylamino ($C_1$–$C_6$)alkyl-, ($C_1$–$C_6$)alkoxy($C_1$–$C_6$)acylamino-, amino($C_1$–$C_6$)acyl-, amino($C_1$–$C_6$)acyl($C_1$–$C_6$)alkyl-, ($C_1$–$C_6$)alkylamino($C_1$–$C_6$)acyl-, (($C_1$–$C_6$)alkyl)$_2$amino($C_1$–$C_6$)acyl-, ($C_3$–$C_{10}$)cycloalkyl($C_1$–$C_6$)alkyl-, ($C_1$–$C_6$)acyloxy($C_1$–$C_6$)alkyl-, ($C_2$–$C_6$)alkoxy($C_1$–$C_6$)alkyl-, piperazinyl($C_1$–$C_6$)alkyl-, ($C_1$–$C_6$)acylamino($C_1$–$C_6$)alkyl-, ($C_6$–$C_{10}$)aryl($C_1$–$C_6$)alkoxy($C_1$–$C_6$)alkyl-, ($C_2$–$C_9$)heteroaryl($C_1$–$C_6$)alkoxy($C_1$–$C_6$)alkyl-, ($C_1$–$C_6$)alkylthio($C_1$–$C_6$)alkyl-, ($C_6$–$C_{10}$)arylthio($C_1$–$C_6$)alkyl-, ($C_1$–$C_6$)alkylsulfinyl($C_1$–$C_6$)alkyl-, ($C_6$–$C_{10}$)arylsulfinyl($C_1$–$C_6$)alkyl-, ($C_1$–$C_6$)alkylsulfonyl($C_1$–$C_6$)alkyl-, ($C_6$–$C_{10}$)arylsulfonyl($C_1$–$C_6$)alkyl-, amino($C_1$–$C_6$)alkyl-, ($C_1$–$C_6$)alkylamino($C_1$–$C_6$)alkyl-, ($C_1$–$C_6$)alkyl(difluoromethylene)-, ($C_1$–$C_3$)alkyl (difluoromethylene)($C_1$–$C_3$)alkyl-, ($C_1$–$C_6$)alkoxy($C_1$–$C_6$)acyl-, ($C_1$–$C_6$)alkylamino($C_1$–$C_6$)acyl-, (($C_1$–$C_6$)alkyl)$_2$amino($C_1$–$C_6$)acyl-, ($C_6$–$C_{10}$)aryl-, ($C_5$–$C_9$)heteroaryl-, ($C_6$–$C_{10}$)aryl($C_1$–$C_6$)alkyl-, ($C_2$–$C_9$)heteroaryl($C_1$–$C_6$)alkyl-, ($C_6$–$C_{10}$)aryl-, ($C_6$–$C_{10}$)aryl($C_6$–$C_{10}$)aryl($C_1$–$C_6$)alkyl- ($C_3$–$C_{10}$)cycloalkyl-, ($C_3$–$C_6$)cycloalkyl($C_1$–$C_6$)alkyl-, ($C_3$–$C_{10}$)heterocycloalkyl-, ($C_3$–$C_{10}$)heterocycloalkyl($C_1$–$C_6$)alkyl-, hydroxy($C_2$–$C_6$)alkyl-, ($C_1$–$C_6$)acyloxy($C_2$–$C_6$)alkyl-, ($C_1$–$C_6$)alkoxy($C_2$–$C_6$)alkyl-, piperazinyl($C_1$–$C_6$)alkyl-, ($C_1$–$C_6$)acylamino ($C_1$–$C_6$)alkyl-, ($C_6$–$C_{10}$)aryl($C_1$–$C_6$)alkoxy($C_1$–$C_6$)alkyl-, ($C_2$–$C_9$)heteroaryl($C_1$–$C_6$)alkoxy($C_1$–$C_6$)alkyl-, ($C_1$–$C_6$)alkylthio($C_1$–$C_6$)alkyl-, ($C_6$–$C_{10}$)arylthio($C_1$–$C_6$)alkyl-, ($C_1$–$C_6$)alkylsulfinyl($C_1$–$C_6$)alkyl-, ($C_6$–$C_{10}$)arylsulfinyl ($C_1$–$C_6$)alkyl-, ($C_1$–$C_6$)alkylsulfonyl($C_1$–$C_6$)alkyl-, ($C_6$–$C_{10}$)arylsulfonyl($C_1$–$C_6$)alkyl-, amino($C_1$–$C_6$)alkyl-, ($C_1$–$C_6$)alkylamino($C_1$–$C_6$)alkyl-, and (($C_1$–$C_6$)alkyl)$_2$amino($C_1$–$C_6$)alkyl.

Further aspects of the invention are described in accord with the Detailed Description of the Invention which follows directly.

DETAILED DESCRIPTION OF THE INVENTION

According to the practice of the present invention, the secretion of growth hormone (GH) from cells (such as those of the anterior pituitary) is facilitated by inhibiting the somatostatin-induced (and G-protein coupled) mechanisms that otherwise naturally act to oppose said secretion. Without being limited as to theory, these somatostatin-induced mechanisms act to oppose both calcium ion and cyclic AMP-mediated signals that otherwise enhance fusion with the cell membrane of cytoplasmic granule structures that contain growth hormone, and thus the subsequent release (secretion) of GH.

The present invention provides an effective approach to the treatment of frailty in older persons, which may be caused, in whole or part, by insufficient levels of growth hormone (GH), or impairment of any of several downstream physiological effects normally associated with growth hormone secretion.

It is generally recognized that GH is important to the maintenance of connective and muscle tissue in adults, and may help, to some extent, to increase muscle mass. Thus growth hormone may be used to assist elderly patients even when growth hormone levels per se are not the cause of, for example, weakness, or attrition of muscle and connective tissues.

The practice of the invention benefits other patients, such as children, when it can be demonstrated that secretion of GH is inadequate, but is subject to enhancement. Deficiency in GH secretion, or resultant GH activity, may arise in several ways. For example, the gene sequence that encodes GH may be expressed in the nucleus at subnormal levels, processing of resultant RNA transcript or nascent polypeptide may be defective, or fusion of cytoplasmic GH storage granules with the cell membrane (with resultant release of GH) may be defective. Additionally, the patient may possess an allele of the GH gene that encodes a mutant protein having less biological activity. Alternatively, there may be an underlying deficiency of GHRH, or a defect in the GHRH receptor, or defects in the the GHRP receptor or deficiency of its endogenous ligand, or in respective signalling mechanisms. Additionally, there may be an excess of somatostatin. In all such cases, the resultant physiological deficiency can be treated by administration of the pharmaceutical compounds of the invention.

In a further aspect of the invention, the performance and growth rate of non-human mammals, such as livestock, is enhanced by appropriate administration of the compounds disclosed herein. Additionally, companion animals, and particularly older companion animals also benefit upon administration of the present compounds.

Under appropriate circumstances, somatostatin antagonists may also exhibit the properties of agonists, and are thus recognized as useful therapeutics in the treamtment of diabetes, for example, see H. Grønbæck et al., *Prog. Basic Clin Pharmacol.* (Basel), 10, pp. 103–128, 1996. Somatostatin agonists are also recognized (see WO 98/44922) as useful therapeutics in the treatment of, for example, diabetic retinopathy, acromegaly, rheumatoid arthritis, neuropathic and visceral pain, irritable bowel syndrome, Crohn's disease, and are useful to inhibit cell proliferation associated with cancer, and to prevent restenosis following angioplasty.

Additionally, sst2 ligands can evidence affinity for other G protein-coupled receptors including the melanocortin receptor, the MCH receptor, and MCR4. It is also expected that sst2 ligands will evidence affinity for the MCH receptor SLC1 (somatostatin-like receptor 1) since it is more than 50% homologous to sst2. Accordingly, the compounds of the present invention are also useful in the treatment of medical conditions mediated through these receptors including, for example, treatment or prevention of obesity, diabetes mellitus, erectile disfuinction and female sexual disfunction. Additionally, the compounds of the present invention are useful to modulate appetite and metabolic rate. In particular, the compounds of the present invention are useful to stimulate the appetite of mammals for the trearment of diseases/disorders associated with inappropriate food intake and weight loss, and for example, to enhance growth and survivability of neonates in livestock.

Although the compounds of the present invention act to indirectly facilitate release of mature growth hormone from the cytoplasmic storage granules of cells, additional therapeutic substances are known that can directly enhance such secretion, and further, can indirectly enhance production of growth hormone by via enhanced expression of GH-encoding DNA in the cell nucleus. In this regard, both growth hormone releasing peptide (GHRP) and growth hormone releasing hormone (also known as growth hormone releasing factor, GHRH/GRF) which act to release GH from cytoplasmic storage granules have been mentioned. Since the release of GH from such granules has been implicated as a signal triggering production of additional GH protein in the cells, it is expected that GH levels may be properly maintained in patients using a "push-pull" approach.

Accordingly, a further preferred example of the invention provides for the co-administration of the somatostain-antagonist compounds of the present invention and GHRP or GHRH, or other substances of like effects. Medical treatment with GHRP (or GHRH) alone is described in the following representative publications: M. Thorner et al., *Journal Of Clinical Endocrinology And Metabolism,* 81(3), pp. 1189–1196, 1996; S. G. Celia et al., *Peptides,* 16(1), pp. 81–86, 1995; M. A. Bach et al., *Journal Of The American Geriatrics Society,* 44(9), S10, 1996; and J. A. Aloi et al., *Journal Of Clinical Endocrinology And Metabolism,* 79(4), pp. 943–949, 1994.

Further, since growth hormone is very labile, and its half-life in the body is very short, it is difficult to provide a safe dosing program for direct administration of growth hormone itself, which avoids wide swings in circulating levels of the hormone. Current sustained release technologies for direct administration of growth hormone can be improved upon. In this regard, the practice of the present invention is particularly valuable to the clinician, since by only indirectly raising GH levels, the hormone's release profile remains, at least in part, under the control of the body's own regulatory feedback systems, and fluctuations in the levels of circulating GH are damped over time. Additionally, the compounds of the present invention may themselves be administered by sustained release mechanisms. It is also recognized that patients sometimes inadvertently skip doses, and various technologies exist to provide continuous dosing via the digestive tract including, for example, osmotic systems. In this regard, the pharmaceutical compositons of the invention are preferably administered according to the technology disclosed in U.S. Pat. No. 4,612,008.

In the preferred practice of the invention, compounds show selectivity for the sst2 receptor compared with other receptor subtypes, for example sst1, sst3, sst4 and sst5. This selectivity minimizes the chance that other molecular biological or biochemical pathways will be adversely affected while growth hormone secretion is being upregulated. Most preferably, the affinity of a compound for the sst2 type receptor should be at least about 10 times greater than for receptors of the other sst-subtypes.

It should be noted that the compounds of the invention may work by more than one mechanism, including those unrelated to interaction at an sst-type receptor, and the utility of the present compounds in the practice of the invention, including for use in treating other disease states not particularly mentioned herein, is not limited by any particular theory as desrcibed herein or by those theories that is generally recognized by those skilled in the art.

Additionally, the compounds of the present invention may interact beneficially with sst-type receptors other than sst2, and may provide therapeutic benefits by acting as somatostatin agonists, rather than antagonists, at sst2 or other sst-type receptors.

As aforementioned, the compounds of this invention include all conformational isomers (e.g., cis and trans isomers, whether or not involving double bonds), tautomers, and all optical isomers of compounds of the formula I (e.g., enantiomers and diastereomers), as well as racemic, diastereomeric and other mixtures of all such isomers.

With respect to the design of the compounds of the invention, particular features involving conformational and optical isomerism are of note.

In connection with the above general formula, particular structural features are of note. In formula 1,

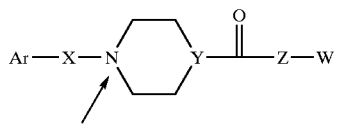

the indicated position is always nitrogen.

When X is $CHR^1$ where $R^1$ is $(C_1-C_6)$alkyl, or is $CR^{1'}R^{1''}$ where $R^{1'}$ and $R^{1''}$ are, independently, $(C_1-C_6)$alkyl groups, it is preferred that the alkyl groups are methyl or ethyl.

Additionally, where substitution by one or more halo groups is permitted above, a preferred example is by two or one halo atoms. Preferably the halo atom(s) is selected from chlorine and fluorine.

With respect to group W, in option(b) thereof, in a preferred example, each of $R^{2'}$, $R^{4'}$ and $R^{5'}$ is hydrogen.

Again with respect to group W, in option (b) thereof, in a preferred example, $R^3$ is selected from option (ii) or option (iii)

(ii)

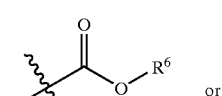

or (iii)

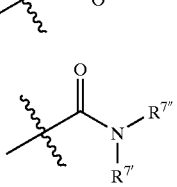

and each of $R^6$, $R^{7'}$ and $R^{7''}$, if present, is $(C_1-C_6)$ alkyl, for example, methyl, ethyl, and t-butyl.

For group Z, selected from the groups consisting of:

A

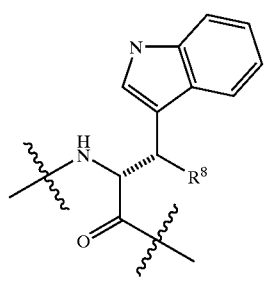

B

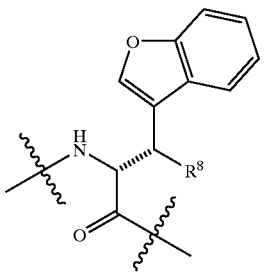

C

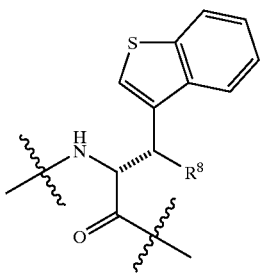

D

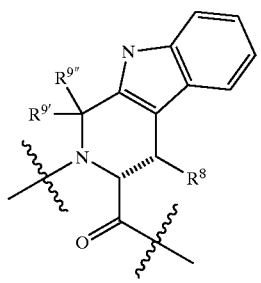

E

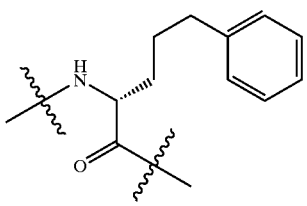

F

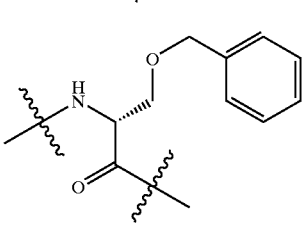

it is preferred that $R^8$, if present, is H, or $(C_1-C_6)$ alkyl, preferably methly or ethyl.

As aforementioned, $R^{9'}$ and $R^{9''}$, if present, are selected from H, $(C_1-C_6)$alkyl, $(C_1-C_9)$heteroaryl$(C_1-C_6)$alkyl, and $(C_6-C_{10})$aryl$(C_1-C_6)$alkyl.

According to a still further embodiment of the invention, group Z may be more broadly defined (group Z') than as otherwise presented herein. In group Z', the exemplified $(C_1-C_9)$heteroaryl groups of Z (that is, indole, benzofuran, and benzothiophene) are subject to replacement by any other $(C_1-C_9)$heteroaryl groups within the definition thereof as aforementioned, which group may be also be optionally substituted. Similarly for group Z', the exemplified $(C_6-C_{10})$ aryl group (phenyl) may be replaced with naphthyl, which may also be optionally substitutued.

In this further embodiment of the invention, attachment of the replacement (C$_1$–C$_9$)heteroaryl group or (C$_6$–C$_{10}$)aryl group to the remainder of the Z' radical may be by more than one bond (see structure D above).

In further compounds of the invention, R$^8$ is (C$_1$–C$_6$) alkyl- or phenyl(CH$_2$)— and said alkyl or phenyl group is optionally substituted by one or more halo or trifluoromethyl groups.

It should also be noted that whenever the term trifluoromethyl is used to describe a moiety of a compound of the invention, said term should also be understood to include any trifluoro(C$_1$–C$_6$)alkyl group, although trifluormethyl is understood to be preferred. Generally also, where substitution by one or more trifluoromethyl groups is permitted, it is preferred that only a single trifluoromethyl group be incorporated.

With respect to the design of the compounds of the invention, particular features involving conformational and optical isomerism are of note. In the below representative structure,

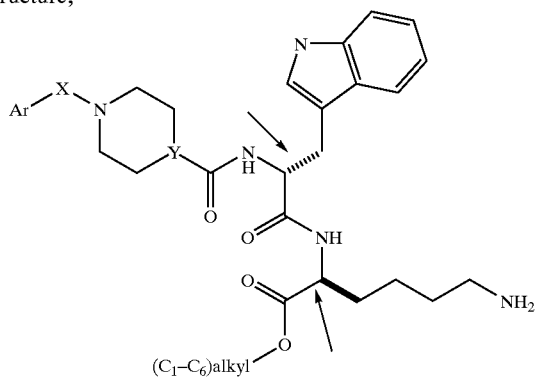

the two arrows indicate chiral centers where it is highly preferred that a particular absolute configuration be maintained. The above compound will be seen to contain a component lysine residue and a component tryptophan residue. In the synthesis of the compound, D-tryptophan and L-lysine were used. It is highly preferred that the absolute configuration contributed by these amino acid optical isomers be maintained, at the positions indicated, in other compounds of the invention, if for example, other Z, W and R groups, and the like, are used.

For example, D-tryptophan can be replaced by D-histidine, a ring-substituted D-tryptophan, or more preferably a structure such as

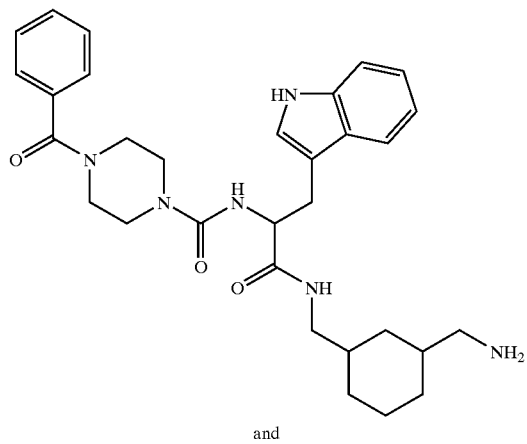

and

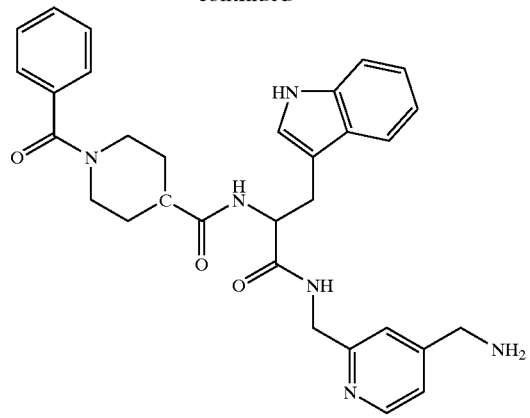

Additionally, many of the groups of the present compounds may be optionally substituted. As aforementioned, such substituents contribute properties useful to production, storage, or use of the inventive compounds as pharmaceuticals, or at least does not substantially negate their pharmacological activity. It will be appreciated that selection of optional substituents is further guided by principles recognized in the art, and/or is capable of validation through the use of the assays described in the present specification.

Pharmaceutical Formulations

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared, for example, by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the present invention that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

In a preferred example of the invention, the compounds of the present invention may be formulated with additional pharmaceutically active substances that directly or indirectly (1) facilitate production and storage in cells of additional growth hormone, or precursor polypeptides thereof, or (2) facilitate release of GH. Such additional substances include growth hormone releasing peptide (GHRP), growth hormone releasing hormone (GHRH), pituitary adenylate cyclase activating polypeptide (PACAP), dopaminergic agonists (e.g. bromocriptine), beta-adrenergic agonists (e.g. isoproterenol) and alpha 1-adrenergic agonists (e.g. methoxamine). For background information see E. O Soyoola et al., *Proceedings of the Society for Experimental Biology & Medicine,* 207(1), pp. 26–33, 1994; V. Locatelli et al., *Pediatric Research,* 36(2), pp. 169–74, 1994; and B. Velkeniers et al., *Journal of Endocrinology,* 143(1), pp. 1–11, 1994.

Equivalently, the additional pharmaceutically active substances may be provided as a separate formulation which is co-administered, or administered at some other timepoint(s) in the course of treatment.

This invention also encompasses pharmaceutical compositions containing prodrugs of compounds of the formula I. This invention also encompasses methods of treating or preventing disorders that can be treated or prevented by decreasing the levels of somatostatin comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

One of ordinary skill in the art will also appreciate that when using the compounds of the invention in the treatment of a specific disease, that the compounds of the invention may be combined with various existing therapeutic agents used for that disease, or for other metabolically related or unrelated disease states that may occur simultaneously. As aforementioned, the additional pharmaceutically active substances may be provided as a separate formulation which is co-administered, or administered at some other timepoint(s) in the course of treatment.

The compounds of the invention can also be used in combination with existing therapeutic agents such as the above-mentioned growth hormone secretagogues for the treatment of growth hormone deficiency.

For the treatment of growth hormone deficiency, the compounds of the invention may be combined with agents such as recombinant growth hormone which is marketed by Genentech and licensees (Neutropin, Genotropin and Protropin), Bio-Technology General and licensees (Zomacton, Growject, Elvetium and SciTropin), Novo Nordisk (Norditropin), LG Chem (Eutropin), Ares Serono (Saizen and Serostim), Eli Lilly Co (Humatrope), Monsanto (Posilac brand of bovine growth hormone) and Alpharma (Reporcin brand of swine growth hormone).

The compounds of the invention can also be used in combination with existing therapeutic agents such as Geref (sermorelin, GHRH) from Serono Laboratories Inc.

The compounds of the invention can also be used in combination with existing therapeutic agents such as anabolic steroids, e.g. androisoxazol androstanolone (DHT, dihydrotestosterone, Stanolone, Anabolex, Andractrim), bolandiol, bolasterone, bolazin, boldenone (Equipoise), calusterone, clostebol (chlortestosterone, Steranabol, Alfa Trofodermin, Dermanabol, Trofodermin, Trofoseptine), danazol (Cyclomen, Danocrine), dehydrochlormethyltestosterone (turinabol, Oral-turinabol), drostanolone (dromostanolone, Drolban, Masterid, Masteril, Masteron, Metormon, Premastril), estradiol, ethylestrenol, fluoxymesterone (Halotestin, Ora-Testryl, Android-F), formebolone, furazabol (Miotolon), mestanolone, mesterolone (Proviron, Pluriviron), methandienone (methandrostenolone, Metaboline), methandriol, methenolone (Primobolan), methyltestosterone (Methandren, Premarin with methyltestosterone, Android, Oreton, Testred, Methyltestosterone tabs, Geri-Bons, Geri-tabs, Dermonal), mibolerone (Cheque), nandrolone (Deca-Durabolin, Durabolin, Nandrabolin, Anabolin, Androlone, Hybolin, Nandrobolic), norclostebol, norethandrolone (Nilevar), oxabolone, oxandrolone (Anavar), oxymesterone (Oranabol), oxymetholone (Anapolon 50, Androyd, Anadrol, Anasteron, Dynasten, Oxitosona, Plenastril, Synasteron, Zenalosyn), penmesterol, prasterone, quinbolone, stanozolol (Winstrol, Winstrol-V, Stromba, Strombaject), stenbolone, testosterone (Malogen, Delatestryl, Malogen, Neo-pause, PMS-testosterone Enanthate, Andriol, Duogex, Neo-Pause, Climacteron, Orchisterone-P, Oreton, Anadiol, Anatest, Testos-100, Heifer-aid, Synovex-H), tibolone, trenbolone (Parabolan, Finaject) or zeranol.

The compounds of the invention can also be used in combination with existing therapeutic agents such as Somazon (mecasermin, recombinant insulin-like growth factor I) from Fujisawa.

For the treatment of older patients with osteoporosis, suitable agents to be used in combination with the compounds of the invention include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib and rofecoxib, analgesics and intraarticular therapies such as corticosteroids and hyaluronic acids such as hyalgan and synvisc.

The compounds of the present invention may also be used in combination with osteoporosis agents such as lasofoxifene, raloxifene, droloxifene or fosomax and immunosuppressant agents such as FK-506 and rapamycin.

The compounds of the present invention may also be used in combination with immunostimulant agents for the treatment of reduced immune function.

The compounds of the present invention may also be used in combination with fertility agents such as human menopausal gonadotropin, chorionic gonadotropin, follicle stimulating hormone, nafarelin, triptorelin, cetrorelix, and ganirelix for the treatment of infertility.

The compounds of the present invention may also be used in combination with AIDS therapies for the treatment of AIDS-related complex.

The compounds of the present invention may also be used in combination with anti-tumor necrosis factor agents such as infliximab (TNF monoclonal antibody) or etanercept (soluble TNF receptor) for the treatment of cachexia.

The compounds of the present invention may also be used in combination with potassium channel blockers, beta-blockers, anticoagulants or vasodilators for the treatment of heart disease.

The compounds of the present invention may also be used in combination with angiotensin II (ATII) antagonists or,erythropoietin for the treatment of renal failure.

For administration to livestock, the compounds of the invention may also be used in combination with feed additives such as antibiotics (e.g. monensin, lasalocid, salinomycin, semduramicin, narasin, maduramicin, virginiamycin, polymixin, efrotomycin, avoparcin, lincomycin, bacitracin, bambermycins, novobiocin, erythromycin, oleandomycin, streptomycin, tylosin, penicillin, tetracycline, oxytetracycline, chlortetracycline, carbadox, olaquindox, neomycin, moenomycin, avilamycin, and flavophospholipol), repartitioning agents, beta-agonists (e.g. Paylean, ractopamine, from Elanco), and also amiterol, bambuterol, bitolterol, broxaterol, buphenine, carbuterol, cimaterol, clenbuterol, clorprenaline, colterol, denopamine, dioxethedrine, dioxifedrine, dobutamine, dopexamine, doxaminol, etanterol, fenoterol, flerobuterol, formoterol, hexoprenaline, ibuterol, imoxiterol, isoetarine, isoxsuprine, levisoprenaline, mabuterol, mesuprine, metaterol, methoxyphenamine, nardeterol, orciprenaline, picumeterol, pirbuterol, prenalterol, procaterol, protokylol, quinprenaline, rimiterol, ritodrine, salbutamol, salmeterol, terbutaline, tretoquinol, tulobuterol, xamoterol and zilpaterol.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation. The active compounds of the invention may also be formulated for sustained delivery.

For oral administration, the pharmaceutical compositions may take the form of, for example, tablets, chewable tablets, or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner, or blended with petfood or animal feed, or as a pre-mix for blending with animal feed.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human is 0.1 to 100 mg of the active ingredient per unit dose which could be administered, for example, 1 to 4 times per day.

Aerosol formulations for treatment of the conditions referred to above in the average adult human are preferably arranged so that each metered dose or "puff" of aerosol contains 20 $\mu$g to 1000 $\mu$g of the compound of the invention. The overall daily dose with an aerosol will be within the range 0.1 mg to 100 mg. Administration may be several times daily, for example 2, 3, 4 or 8 times, giving for example, 1, 2 or 3 doses each time.

Injected doses are preferably administered from about once a month, up to about 1 to 4 times per day, at an individual dosing of 0.01–1 mg/kg (of active ingredient) and may be intramuscular, intravenous, or subcutaneous, for example.

As is well recognized, the precise dose, and method and timing of administration thereof, are capable of determination by those skilled in the art, and depend upon numerous factors including the activity of the therapeutic compound, the properties of the formulation thereof, the nature and location of the target tissue, and the particulars of the disease state as it exists in a particular patient. Additionally, when the compounds of the present invention are administered to a patient with additional pharmaceutically active substances, one or more pharmaceutical compositions may be used to deliver all of the active agents, which may be administered together, or at different times, as determined by those skilled in the pharmaceutical or medical arts.

The following reaction schemes illustrate preparation of compounds of the present invention. It will be appreciated that certain groups represented by letters ("R" groups, and the like) in the Schemes do not always correspond with similarly defined component groups of the formula (I) compounds themselves, since certain functionalities of the reactants are modified, by definition, when the products are formed. For example, $Ar^2$ corresponds to the appropriate portion of any group Z of formula (I) as defined above, keeping in mind that group Z may also be defined as group Z', as above. $R_3$ typically represents a $(C_1-C_6)$alkyl group, whether primary, secondary, or tertiary, but can also be other groups such as $(C_6-C_{10})$aryl or benzyl, for example. Group $Ar^1$ corresponds to the definition of group Ar formula (I). Group X is as defined in formula (I).

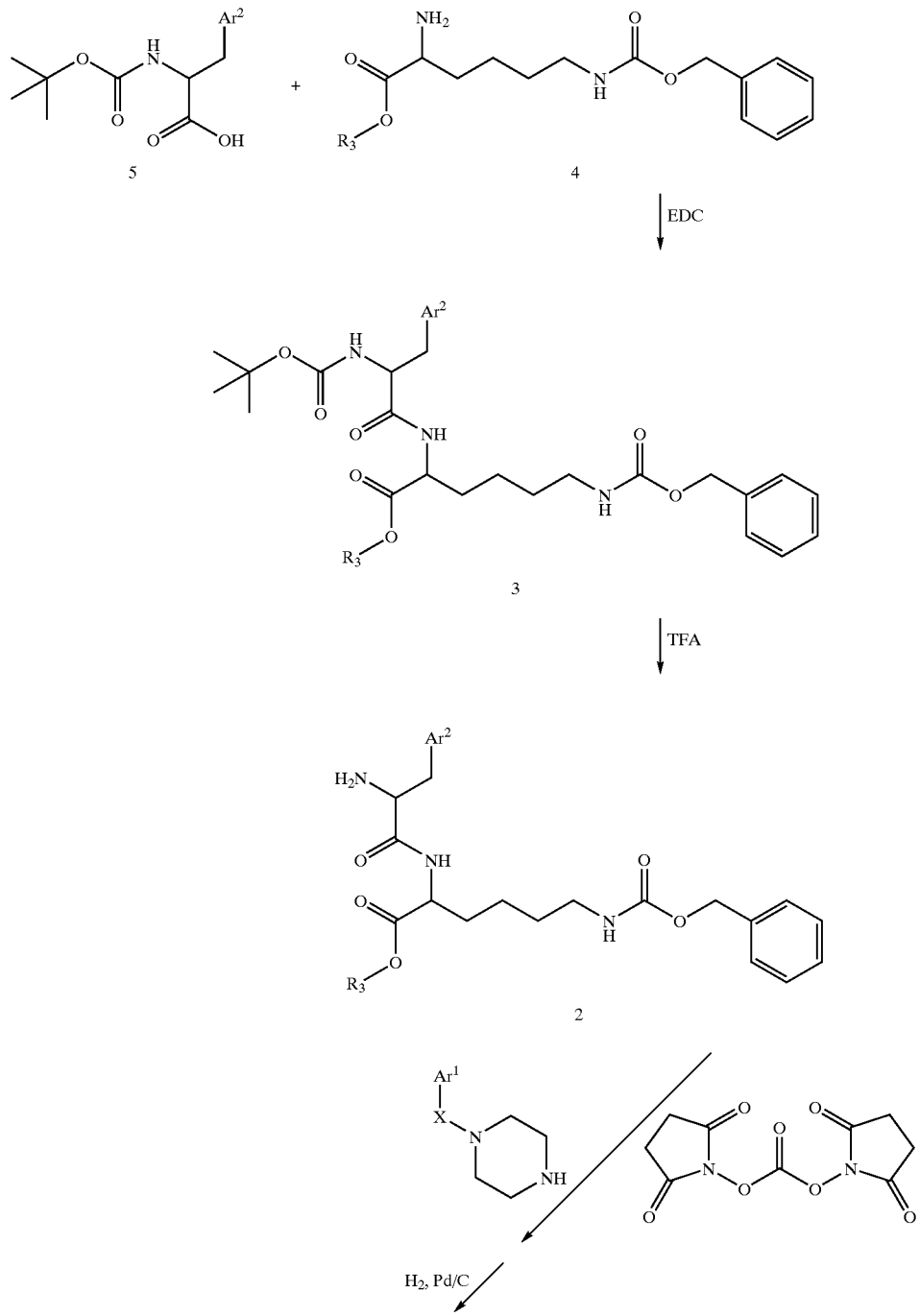

-continued
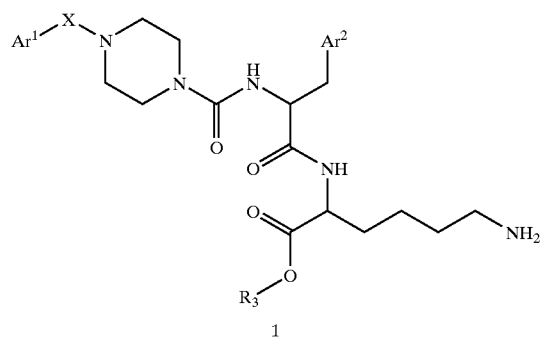
Scheme 1B
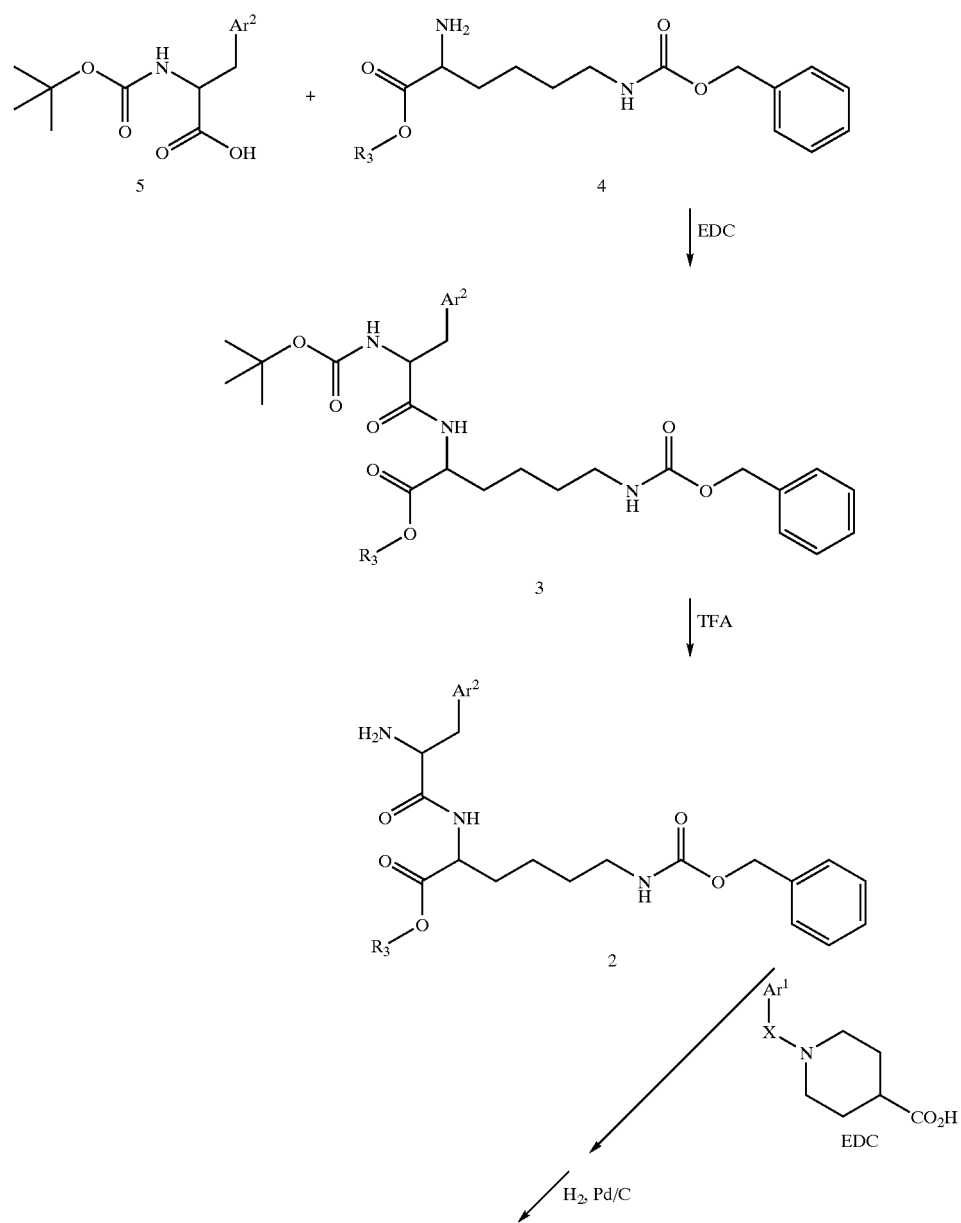

-continued
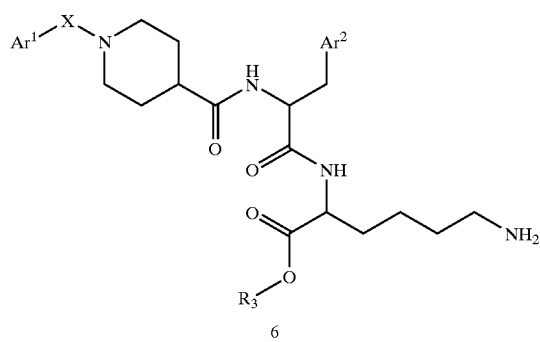
6
Scheme 2A
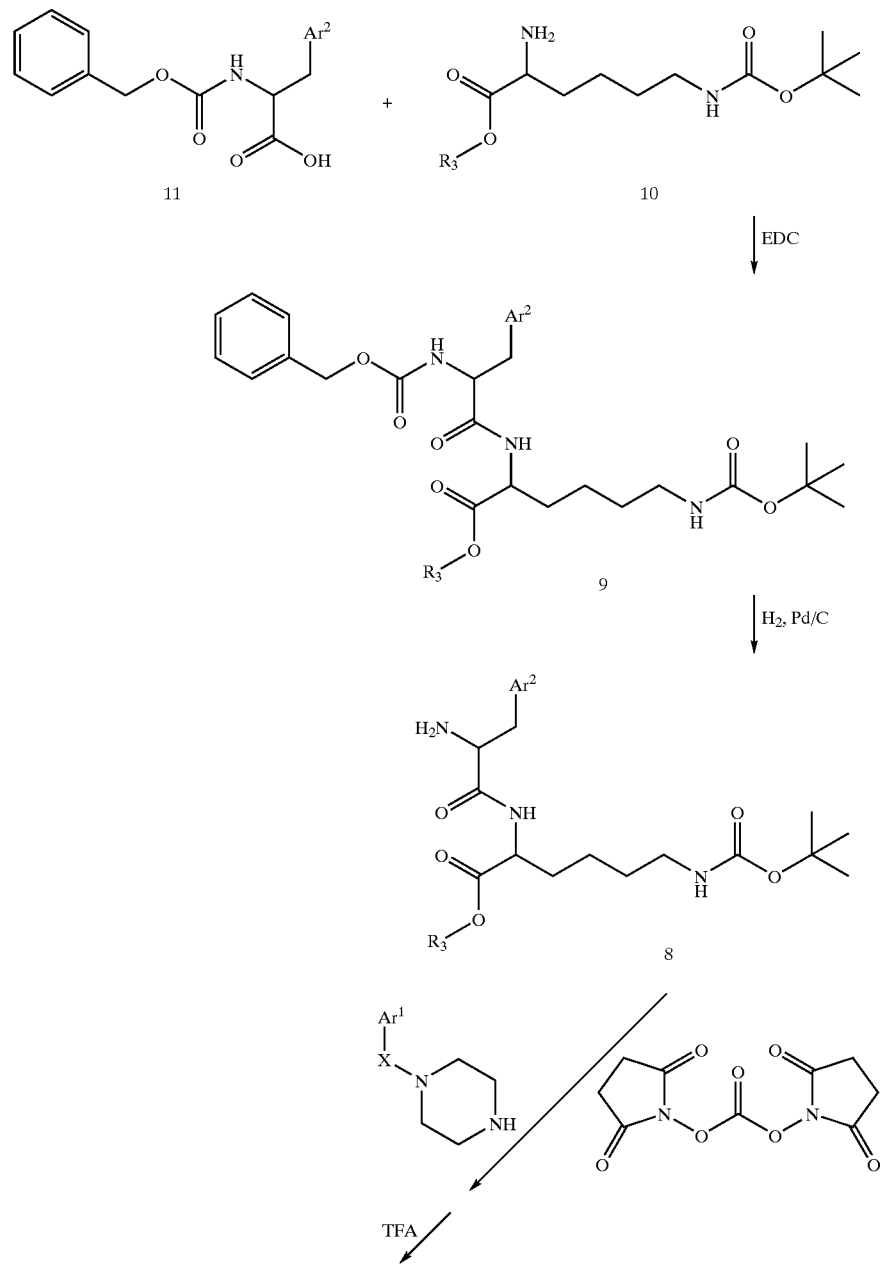

-continued
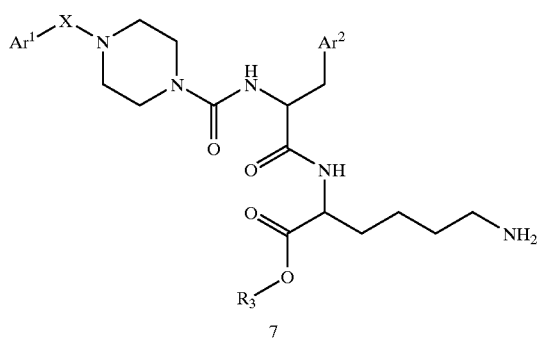
7
Scheme 2B
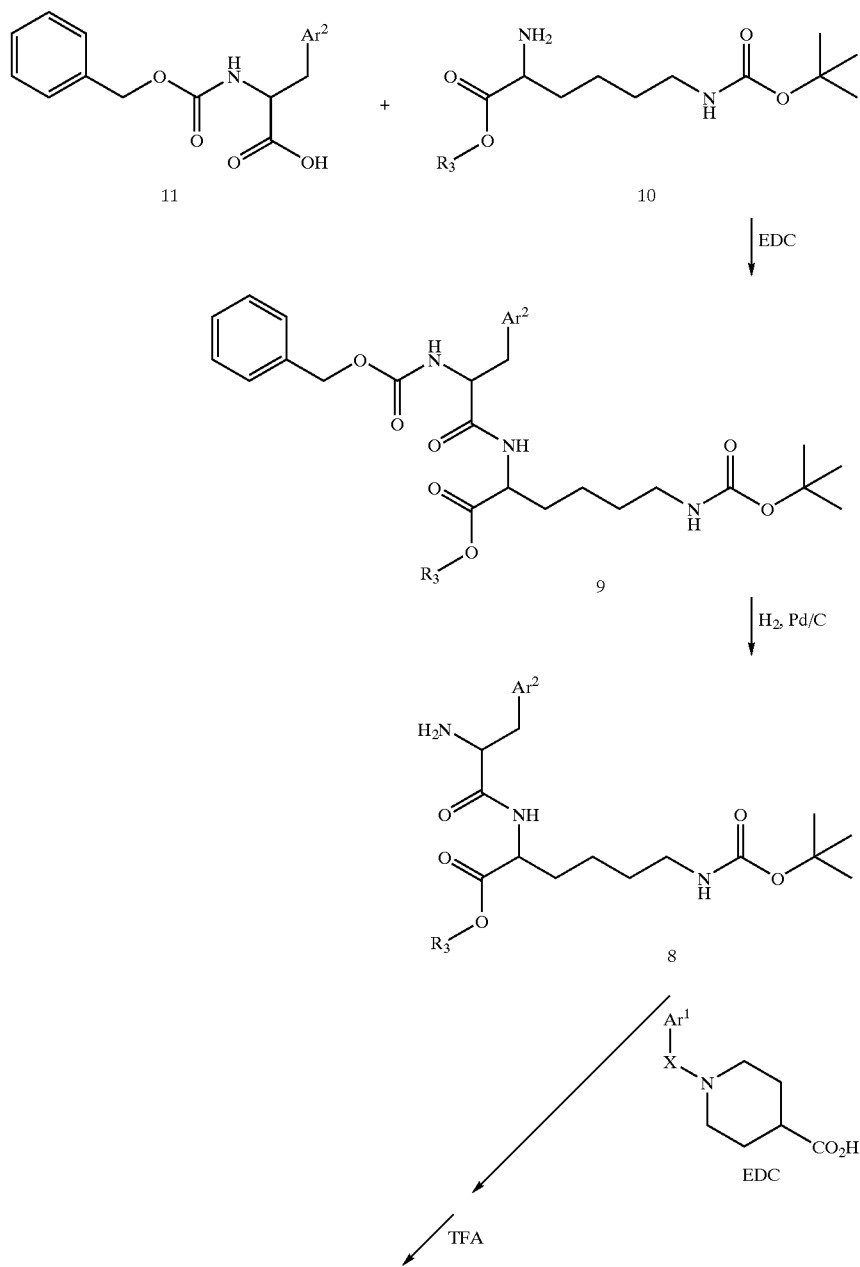

-continued

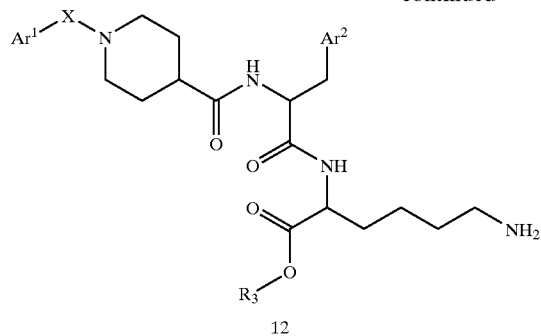

12

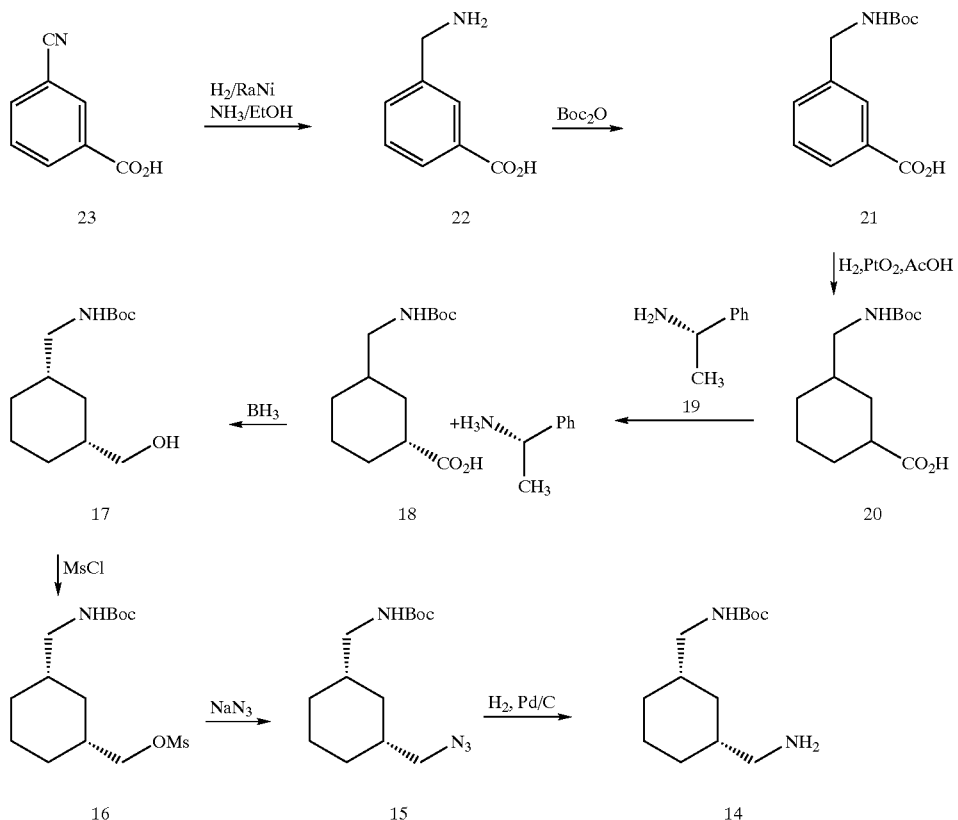

Scheme 3A

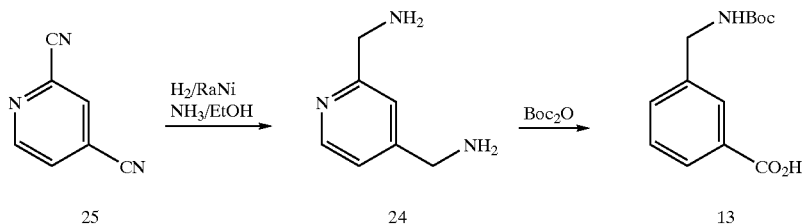

Scheme 3B

General reaction conditions

Generally speaking, the compounds of the present invention are made by a series of condensation reactions in which certain reactive groups are appropriately protected, and the sequence of condensation is controlled. Schemes 1A versus 2A (piperazines), and IB versus 2B (piperidines) demonstrate alternative pathways to the same products. In these Schemes, compounds such as 5 (BOC derivatives) and 11 (CBZ derivatives) are readily prepared or are commercially available. Preparation thereof with numerous $Ar^2$ groups (as defined for group Z or Z') will be immediately apparent to those skilled in the art.

Similarly, the reactants that provide the piperazine and piperidine moieties in Schemes 1 and 2 are themselves readily prepared with all the variety of Ar¹ or X groups permitted in the practice of the invention.

A description of representative reaction sequences is provided in Examples 1–4.

Schemes 3A and 3B provide approaches to group "W" in the general structure of formula (I), where W is alternative (a),

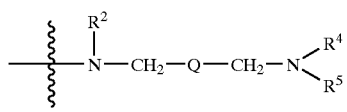

and in particular, outline representative syntheses of component W wherein Q is, for example, either cyclohexane or pyridine. Thus, Schemes 3A and 3B permit synthesis of compounds analogous to compounds 1, 6, 7, and 12, and similar compounds of Schemes 1 and 2, wherein the representative lysine moiety thereof is replaced by a moiety that includes a cyclohexane or pyridine group, for example. Numerous equivalent schemes are available to the practitioner.

Referring to Scheme 3A, compounds of formula 14 may be prepared from compounds of 15 by reduction with hydrogen under appropriate conditions. Compounds of formula 15 may be prepared from compounds of formula 16 via reaction using NaN₃ to displace the mesylate ester of compounds 16. Compounds 16 may be prepared from compounds 17 with mesyl (methanesulfonyl) chloride under basic conditions, for example, in triethylamine/dichloromethane at 0° C., in good yield. Compounds 17 may be prepared from compounds 18 by reduction at the carboxyl group thereof using BH₃Compounds 18, having the stereospecificity indicated in Scheme III(a), are prepared from racemic compounds 20 by chiral resolution with stereospecific α-methylbenzylamine, followed by selective purification, such as by crystallization. Compounds 20 may be prepared from the corresponding aromatic compounds 21 by reduction with hydrogen, for example, under appropriate conditions. Compounds 21 in turn are prepared from the corresponding (unprotected) compounds 22 by reaction with BOC anhydride under standard conditions. Finally, compounds 22 may be prepared from available starting materials 23, by reduction of the cyano group with hydrogen over a Raney nickel preparation. In Scheme III(b), advantage is taken of available starting materials to generate compounds of the formula 14' in 2 steps, first from compounds of formula 24 using BOC anhydride. Compounds 24 are generated from compounds of formula 25 by reduction of both cyano groups, again with hydrogen and Raney nickel as catalyst.

EXAMPLES

The following are representative compounds of the invention

Example 1

Synthesis of Certain Intermediates

CBZ-D-Trp-Lys(OtBu)-otBu

The following synthetic step is also evidenced in Scheme 2A., referring to reaction of compounds of types 11 and 10 therein, in order to form an intermediate 9. "CBZ" refers to phenyl-(CH₂)—O—C(O)—, the carbobenzyloxy group.

To a solution of 406 mg of CBZ-D-Trp-OH (1.2 mmol), 302 mg of Lys(BOC)-OtBu HCl (1.0 mmol), 202 mg of hydroxybenzotriazole (1.5 mmol) and 366 mg of 4-dimethylaminopyridine (3 mmol) in 60 mL of methylene chloride was added 448 mg (1.5 mmol) of 1,3dimethylaminopropyl-3-ethylcarbodiimide hydrochloride (EDC). After stirring for 3 hours 100 mL more methylene chloride was added to the reaction, and it was washed four times with 25 mL portions of 0.1 N hydrochloric acid solution, twice with 25 mL of 50% saturated sodium bicarbonate solution, once with 50 mL of saturated brine, dried over anhydrous magnesium sulfate, filtered, and the solvent removed under reduced pressure to yield 590 mg (100%) of CBZ-D-Trp-Lys(BOC)-OtBu.

D-Trp-Lys(CBZ)-OtBu

A solution of 590 mg of CBZ-D-Trp-Lys(OtBu)-OtBu was hydrogenated at 50 PSI for 2.5 hours in 50 mL of methanol with 100 mg of 10% palladium on carbon catalyst. The catalyst was then filtered off and the solvent evaporated to yield 466 mg (95%) of D-Trp-Lys(BOC)-OtBu (see Scheme 2A, reactants 9→8).

Example 2

Synthesis of 6-Amino-2-(3-(1H-indol-3-yl)-2-{[4-(toluene-4-sulfonyl)-piperazine-1-carbonyl]-amino}-propionylamino)-hexanoic acid tert-butyl ester (a) BOC-D-Trp)-Lys(CBZ)-OtBu To a solution of 1.52 gm of BOC-D-Trp (5 mmol), 1.89 gm of Lys(Z)-OtBu HCl (5 mmol), 1.01 gm of hydroxybenzotriazole (7.5 mmol) and 1.83 gm of 4-dimethylaminopyridine (15 mmol) in 450 mL of methylene chloride was added 2.22 gm (11.6 mmol) of 1,3-dimethylaminopropyl-3-ethylcarbodiimide hydrochloride. After stirring for 15 hours 300 mL more methylene chloride was added to the reaction, and it was washed four times with 100 mL portions of 50% saturated aqueous citric acid solution, once with 100 mL of 50% saturated sodium bicarbonate solution, once with 100 mL of saturated brine (NaCl), dried over anhydrous magnesium sulfate, filtered, and the solvent removed under reduced pressure to yield 2.95 gm (94%) of BOC-D-Trp-Lys(CBZ)-OtBu. (see Scheme 1A, for reaction of reactants 5 and 4→3).

(b) D-Trp-Lys(CBZ)-OtBu

To a solution of 2.95 gm of BOC-D-Trp-Lys(CBZ)-OtBu (4.7 mmol) in 200 mL of methylene chloride was added 10 mL of trifluoroacetic acid. The reaction (see Scheme 1A, for reaction of 3→2) was stirred for 2 hr, and the solvent was rapidly removed under reduced pressure at less than 35 C. The oil was partitioned between 300 mL of methylene chloride and 100 mL of 50% saturated aqueous sodium bicarbonate solution. The layers were separated, the organic layer was washed with 100 mL of saturated brine, dried over anhydrous magnesium sulfate, filtered, and the solvent removed under reduced pressure to yield 2.50 gm (100%) of D-Trp-Lys(CBZ)-OtBu.

(c) 6-Benzylozycarbonylamino-2-(3-(1H-indol-3-yl)-2-{[4-(toluene-4-sulfonyl)-perazine-1-carbonyl]-amino}-propionylamino)-hexanoic acid tert-butyl ester To a solution of 523 mg of D-Trp-Lys(CBZ)-OtBu (1.00 mmol) and 129 mg (1.00 mmol) of diisopropylethylamine in 40 mL of anhydrous methylene chloride and 80 mL of anhydrous tetrahydrofuran was added 256 mg (1.0 mmol) disuccimidylcarbonate. After stirring for 2 hours the starting material was gone by TLC (9:1:0.2 chloroform:methanol:triethylamine), and 264 mg of tosylpiperazine (1.10 mmol) in 5 mL of anhydrous methylene chloride was added. The reaction was stirred for 15 hours, then 300 mL of methylene chloride was added and it was washed three times with 50 mL portions of 50% saturated aqueous citric acid solution, once with 100 mL of saturated brine, dried over anhydrous magnesium sulfate, filtered, and the solvent removed under reduced pressure to yield 858 mg of crude product. This was flash chromatographed with 2:1 ethyl acetate:hexane as eluent to yield 550 mg (70%) of the pure intermediate product, 6-Benzylozycarbonylamino-2-(3-(1H-indol-3-yl)-2-{[4-(toluene-4-sulfonyl)-piperazine-1-carbonyl]-amino}-propionylamino)-hexanoic acid tert-butyl ester. (see Scheme 1A, for reaction of reagent 2).

(d) Final Product

A solution of 1.100 gm of the product from above was hydrogenated at 50 PSI in 60 mL of methanol with 110 mg of 10% palladium on carbon catalyst. After 2 hr. the reaction was not complete by TLC (9:1 chloroform:methanol), so another 110 mg of catalyst and 10 mL of methanol were charged to the mixture, and the hydrogenation continued for another 2 hr, at which time the reaction was complete. The catalyst was filtered off, and ~20 mL of 0.1 N aqueous hydrochloric acid was added to bring the pH to 2.0. The soultion was then lyophilized to yield 500 mg (52%) of 6-Amino-2-(3-(1H-indol-3-yl)-2-{[4-(toluene-4-sulfonyl)-piperazine-1-carbonyl]-amino}-propionylamino)-hexanoic acid tert-butyl ester. (see Scheme 1A, for formation of product 1).

$^1$H NMR (CD$_3$OD): δ4.50 (1H, t, J=7 hz), 4.21 (1H, m), 2.49 (3H, s), 1.44 (9H, m). MS: M+1=655. Other substituted piperazines could be used in the third step of this sequence to yield additional products.

Example 3

6-Amino-2-[2-[(1-benzenesulfonyl-piperidine-4-carbonyl)-amino]-3-(1H-indol-3-yl)-propionylamino]-hexanoic acid tert-butyl ester A solution of 80.0 mg of D-Trp-Lys(CBZ)-OtBu (0.164 mmol), 33.2 mg of hydroxybenzotriazole (0.246 mmol) and 60.0 mg of 4-dimethylaminopyridine (0.492 mmol) in 40 mL of methylene chloride was split into 4 portions of 10 mL each. To one 10 mL portion was added 16.5 mg (0.0615 mmol) of benzenesulfonylisonipecotic acid and 18.0 mg (0.0615 mmol) of 1,3-dimethylaminopropyl-3-ethylcarbodiimide hydrochloride. After stirring for 2 hours 15 mL more methylene chloride was added to the reaction, and it was washed four times with 10 mL portions of half saturated citric acid solution, twice with 10 mL of 50% saturated sodium bicarbonate solution, once with 10 mL of saturated brine, dried over anhydrous magnesium sulfate, filtered, and the solvent removed under reduced pressure. The residue was then dissolved in 5 mL of methylene chloride and 250 µL of trifluoroacetic acid was added with stirring.

The reaction was followed closely by TLC (9:1 Chloroform:methanol). After 2 hours it was judged to be complete, and the solvent was removed rapidly under reduced pressure. The residue was triturated with diethyl ether and dried to yield 32 mg (100%) of the pure triflouroacetic acid salt of 6-Amino-2-[2-[(1-benzenesulfonyl-piperidine-4-carbonyl)-amino]-3-(1H-indol-3-yl)-propionylamino]-hexanoic acid tert-butyl ester.

$^1$H NMR (CD$_3$OD): δ4.68 (1H, m), 4.22 (1H, m), 1.45 (9H, m). MS: M+1=640.

Example 4

6-Amino-2-[2-[(4-benzenesulfonyl-piperazine-1-carbonyl)-amino]-3-(1H-indol-3-yl)-propionylamino]-hexanoic acid tert-butyl ester A solution of 40.0 mg of D-Trp-Lys(CBZ)-OtBu (0.082 mmol), 15.8 mg of N,N-diisopropylethylamine (0.123 mmol) and 21.0 mg of N,N-disuccimidyl carbonate (0.082 mmol) in 4 mL of methylene chloride and 4 mL of tetrahydrofuran was stirred at room temperature for 15 hours. The solution was then split into 4 equal portions of 2.0 mL each. To one 2.0 mL portion was added 4.6 mg (0.0205 mmol) of benzenesulfonylpiperazine in 1.0 mL of tetrahydrofuran. After stirring for 24 hours 10 mL more methylene chloride was added to the reaction, and it was washed twice with 5 mL portions of 0.1 N hydrochloric acid solution, once with 5 mL of saturated brine, dried over anhydrous magnesium sulfate, filtered, and the solvent removed under reduced pressure. The residue was then dissolved in 2 mL of methylene chloride and 100 □L of trifluoroacetic acid was added with stirring. The reaction was followed closely by TLC (9:1 Chloroform:methanol). After 0.5 hours it was judged to be complete, and the solvent was removed rapidly under reduced pressure. The residue was triturated with diethyl ether and dried to yield 11 mg (71%) of the pure trifluoroacetic acid salt of 6-Amino-2-[2-[(4-benzenesulfonyl-piperazine-1-carbonyl)-amino]-3-(1H-indol-3-yl)-propionylamino]-hexanoic acid tert-butyl ester. Other substituted piperazines could be used in this step to yield additional products.

$^1$H NMR (CD$_3$OD): δ4.50 (1H, t, J=7 hz), 4.21 (1H, m), 1.44 (9H, m). ms: m+1=641.

Example 5

6-Amino-2-[2-[(4-benzoyl-piperazine-1-carbonyl)-amino]-3-(1H-indol-3-yl)-propionylamino]-hexanoic acid tert-butyl ester $^1$H NMR (CD$_3$OD): δ4.62 (1H, t, J=8 hz), 4.25 (1H, m), 2.83 (2H, t, J=8 hz), 1.48 (9H, m). MS: M+1=605.

Example 6

6-Amino-2-(3-(1H-indol-3-yl)-2-{[4-(4-methyl-benzoyl)-piperazine-1-carbonyl]-amino}-propionylamino)-hexanoic acid tert-butyl ester $^1$H NMR (CD$_3$OD): δ4.62 (1H, t, J=7 hz), 4.25 (1H, m), 2.83 (2H, t, J=7 hz), 2.42 (3H, s), 1.48 (9H, m). MS: M+1=619.

Biological Assays

Various types of somatostain agonists are well known in the art, and the capacity of a compound of the present invention to act as an agonist, an antagonist, or as either, depending on physiological circumstances, can be predicted from the assays which are known in the art and/or described below. For example, measurement of cyclic-AMP, growth hormone release, microphysiometry responses, cell proliferation or protein kinase activity can be measured in cultured pituitary cells, cell lines or other cells such as neuroblastoma cells that express somatostatin receptors, and cells transfected with recombinant somatostatin receptorsincluding transfected yeast cells. (Y. C. Patel et al., *Biochemical & Biophysical Research Communications,* 198(2), pp. 605–612, 1994; M. G. Cattaneo et al., *FEBS Letters,* 397 (2–3), pp. 164–168, 1996; J. A. Koenig et al., *British Journal of Pharmacology,* 120(1), pp. 45–51, 1997; D. Djordjijevic et al., *Endocrinology*, 139(5), pp. 2272–2277, 1998; W. R. Baumbach et al., *Molecular Pharmacology*, 54(5), pp. 864–73, 1998.

Generally, somatostatin or agonists thereof demonstrate inhibitory activity, hence a stimulus is first applied (e.g. forskolin for cyclic-AMP) and the inhibitory effect of somatostatin observed. Antagonists reverse the inhibitory effects of somatostatin.

The ability of compounds of formula (I), and the pharmaceutically acceptable salt, solvates or hydrate thereof (hereinafter referred to as the compounds of the present invention) to act as somatostatin antagonists, or agonists, and consequently to demonstrate their effectiveness in the treatment of disease states, is shown by the following assays.

Example 7

Bovine ("b")sst2 Binding Assay

The present example describes an assay for binding of pharmaceutically useful somatostatin agonists and antagonists at the bovine sst2 receptor.

Referring to the detailed protocols which follow, the methods for culturing Neuro2A cells and measuring competitive binding potency ($IC_{50}$) were similar to those described by J. A. Koenig et al., "Somatostatin receptors in Neuro2A neuroblastoma cells: operational characteristics", *British J. Pharmacol.*, 120, 45–51, 1997, with the following modifications.

Binding assays were conducted 72 hours after transiently transfecting the Neuro2A cells with a plasmid (PCI-bsst2) containing an insert coding for the bovine sst2 receptor, placed downstream of the cytomegalovirus promoter. In the transfection step, $6.5 \times 10^6$ Neuro2A cells were added in 35 ml of media to each tissue culture flask (162 cm$^2$ surface area). The next day, transfection was conducted using Fugene 6 (Boehringer Mannheim, 1 814 443) according to the manufacturer's directions. The Fugene 6 (30 μl/flask) was equilibrated with 8 μg of PCI-bsst2 plasmid, and added to the Neuro2A cells in the absence of fetal bovine serum. After 3 hours, fresh serum-containing media was added. The assay buffer was modified to contain 50 mM HEPES, 5 mM MgCl$_2$, 1 mg/ml bovine serum albumin (BSA), 0.02 mg/ml bacitracin, and 10 μM each of aprotinin, leupeptin and AEBSF. The transfected Neuro2A cells were dissociated in the absence of trypsin/EDTA, in ice cold assay buffer (5.5 ml/flask), and cells were homogenized in a 55 ml Wheaton Dounce homogenizer (15–20 strokes). Membrane preparations were stored in aliquots at $-70°$ C. Competitive binding assays and separation of bound from free radioactivity were conducted in polyethyleneimine-soaked Millipore 96 Well GF/C Filterplates, (MAFC NOB10). An amount of membrane was used that bound approximately 20% of [$^{125}$I]-somatostatin 14 tracer (Amersham, IM161), which was added to all wells at 15,000 cpm/well (approximately 15 nCi/well). Somatostatin was included in each experiment as positive control, at 7 concentrations from 0.0042 to 1.667 nM, and test compounds were included at 7 concentrations from 33 nM to 13.33 μM. The reaction volume was 300 μl and the incubation was conducted for 1 hour at 37° C. Non-specific binding was defined using 0.83 μM somatostatin 14. The incubation was terminated by vacuum filtration through the glass fiber plate bottom, followed with a 250 μl wash with assay buffer minus BSA and protease inhibitors. The plate bottom was then sealed, scintillation fluid was added (Wallac Supermix, 250 μl/well), and radioactivity was measured in a 96 well microtiter liquid scintillation counter. Accordingly, a detailed description of a preferred protocol is as follows.

Buffers & solution

Wash Buffer (per liter):
50 mM HEPES, 50 ml of 1 M stock (Gibco BRL #15630-080)
5 mM MgCl, 0.476 g (Sigma M-8266)
  pH to 7.4 with HCl or KOH
Bring to 1 liter with ddH$_2$O.
0.2% Polyethylenimine filter prewet solution (per liter):
4 g Polyethylenimine 50% aqueous solution (P-3143 Sigma)
Bring to 1 liter with ddH$_2$O
Binding Buffer (per liter):
50 mM HEPES, 50 ml of 1M stock (Gibco BRL #15630-080)
5 mM MgCl, 0.476 g (Sigma M-8266)
  pH to 7.4 with HCl or KOH
1 g Bovine Serum Albumin (A-7888 Sigma)
20 mg Bacitracin (B-0125 Sigma)
10 μM Aprotinin (A-4529 Sigma)
10 μM Leupeptin (L-8511 Sigma)
10 μM AEBSF (Sigma A-8456)
Bring to 1 liter with ddH$_2$O.
Culture Media (per 500 ml):
DMEM, supplemented with 10% Fetal bovine serum, and penicillin/streptomycin (pipette 55 ml FBS, 5.5 ml penn/strep into 500 ml container).

Materials List

1. MgCl$_2$ (Sigma M-8266)
2. 1M HEPES (Gibco BRL cat #15630-080)
3. Bacitracin (B-0125 Sigma)
4. Aprotinin (A4529 Sigma)
5. Leupeptin (L-8511 Sigma)
6. Bovine Serum Albumin (Sigma cat #A-7888)
7. Dulbecco's PBS Gibco BRL (cat #14040-141)
8. Cell dissociation buffer (Gibco BRL cat #13150-016)
9. 50% Polyethylenimine (Sigma P-3143)
10. Neuro 2A (ATCC, Manassas, Va., CCL #131) mouse neuroblastoma cell line
11. CMV-bsst2 plasmid for transient transfection, carrying a bovine("b")sst2-encoding region
12. Fugene 6 transfection reagent (Boeringer Mannheim cat #1 814 443)
13. Titer plate shaker (Lab Line Instruments Inc.)
14. Millipore glass fibre filter type C 96 well plates (MAFC NOB10)
15. Millipore vacuum plate device
16. Matrix polypropylene 1 ml 96 well block (8100-96)
17. tabletop centrifuge w 50 ml tube holders
18. Ice
19. 50 ml sterile conical tubes
20. Wallac radioactive Betaplate & Lumenometer counter (Jet 1450 microbeta)
21. Wallac scintillation fluid-optiphase 'Supermix' (1200-439)
22. Millipore plate sealers (MATA09600)
23. 162cm$^2$ vented tissue culture plates (Costar #3151)
24. Amersham 1251 SRIF-14 (Tyr-11) (Amersham #IM161)
25. DMEM (Gibco BRL cat #11965-092)
26. FBS Gemini Bio-products (Cat #100-107, lot #A1801N)
27. Penicillin-streptomycin (Gibco BRL cat #15140-122)
28. "Cold" SRIF-14 (Sigma S-1763)
29. AEBSF (Sigma A-8456)
30. Dimethyl Sulfoxide A.C.S. grade (JT Baker cat #9224-01)

Preparation of Plasmid with bsst2 Encoding DNA

1. Innoculate 300 ml of LB/amp media with a single colony of cells carrying PCI-bsst2 plasmid. Allow the cells to grow a full 24 hours, and then pellet the cells by centrifugation. A Qiagen plasmid purification protocol (Mega protocol) is used. At end of protocol, wash the DNA with 70% ethanol two more times to insure clean DNA. The DNA prep is then allowed to air dry, followed by resuspension in 1 ml of molecular biology grade 10 mM Tris-HCl pH=7.4. DNA concentration is quantitated using a spectrophotometer. Although the yield will change, the concentration of PCI-bsst2 plasmid should be approximately 1 ug/ul. A concentration lower than about 0.3 ug/ul could interfere with the following transfection protocol and, in such case, concentrating the plasmid might be required.

Preparation of Neuro 2A Cells & Transient Transfection of bsst2 Plasmid

1. Grow Neuro 2A neuroblastoma to confluence in a 162 cm$^2$ vented tissue flask in DMEM (Gibco BRL cat #11965-092), 10% FBS, and 100 units Pen G sodium, 100 ug/ml strep sulfate (penicillin/streptomycin (Gibco-Brl #15140-122)=5.5 ml per 550 ml culture buffer) at 5% CO2, 37° C.
2. Cells are washed once with 13 ml of 37° C. Dulbeccos PBS.
3. Cells are harvested by adding 3 ml of dissociation buffer (Gibco BRL cat #13150-016), and incubating for 5 min. at 5% $CO_2$, 37° C. (Do not use trypsin). Bang the flasks on their side to dissociate cells from flask, add 10 ml culture media, and pipette into sterile 50 ml polypropylene conical tubes.
4. Centrifuge at 1000 rpm for 5 minutes at room temperature to pellet cells.
5. Remove media and resuspend cells in culture media. Titurate to disperse cells into single cell dispersion. Inoculate into new 162 cm$^2$ vented tissue flasks, splitting 1:5 (approximate seeding is 6.5×10$^6$ cells per 162 cm$^2$ flask.
6. Add 35 ml culture media per 162 cm$^2$ vented tissue flask.
7. Allow cells to adhere and grow overnight (16–18 hours) at 5% $CO_2$, 37° C. Cells are ready for transfection (about 50% confluency).
8. Per 162 cm$^2$ flask, pipette 470 ul of DMEM (no FBS), Penn/Strep into a 15 ml sterile polypropylene conical tube. Directly add 30 ul of Fugene 6 transfection reagent (Boeringer Mannheim cat #1 814 443) to the media and allow to equilibrate for 5 minutes (add directly to media, do not pipette to side of tube). In a separate 15 ml conical sterile tube add 8 ug of PCI-bsst2 plasmid to bottom of tube (this should be no more than 20 ul). Pipette all of the 500 ul of DMEM/Fugene mixture directly onto DNA and equilibrate at room temperature for 15 minutes. The reagent will form liposomes carrying DNA plasmid molecules. Add full mixture directly to the media of each 162 cm$^2$ vented tissue flask containing approximate 50% confluent Neuro 2A cells and incubate 3 hours at 5% $CO_2$, 37° C. (at this stage, the FBS in media will no longer interfere with the transfection). Remove the media and add 35 ml fresh culture media to cells.
9. After 72 hours post transfection, harvest cells as described above in steps 2–4. Remove media from cells and freeze cells in the polypropylene conical tube by placing in freezer at –80° C. Accumulate enough cells to make large batches of membrane (approximately 80 flasks).

Preparation of Cell Membrane of Neuro2A Cells Expressing bSST$_2$ Receptor

1. Resuspend transfected cells by adding 5.5 ml ice cold binding buffer (see above for formula) per flask of bSST$_2$ transfected Neuro 2A cells. Vortex cells to yield a single cell suspension.
2. Using a 55 ml Wheaton Dounce cell tissue homogenizer, homogenize all cells (15–20 strokes) and combine into a large batch. Save in a 3 ml aliquots (enough for one 96 well plate)and freeze at –70° C. A membrane titration will have to be done to determine exact amount of membrane to add per well.

Preparation of ($^{125}$I) Somatostatin (SRIF)

Amersham $^{125}$I SRIF (#IM161) is provided in 50 uCi bottles. Each 50 uCi bottle is diluted into 10 ml binding buffer and stored in 330 ul aliquots at –20° C. Each aliquot is diluted to 11 ml with binding buffer directly before assay. This is enough for one 96-well plate.

Millipore 96 Well GF/C Filterplate Preparation

Pipette 100 ul of a 0.20% Polyethylenimine/$H_2O$ solution into each well of a 96 well plate, and incubate for at least 2 hours. Liquid is then removed by vacuum filtration and the plate is set out to dry overnight. Dried plates are stored at RT in a box indefinitely.

Membrane Titration of Neuro2A/bSST$_2$ Membrane

In order to normalize batches of membrane as much as possible, a membrane titration is performed:

Approximately 15,000 CPM of fresh diluted SRIF-14 (125-I) is pipetted into every well. Various volumes of membrane are added (10,20,40 & 80 ul) into triplicate wells. The same volumes of membrane and 1 uM Cold SRIF-14 are added into triplicate wells to ascertain non-specific binding. Additionally, each volume of membrane is titrated with cold SRIF-14 from 0.03 nM–5 nM to obtain an IC50 for cold SRIF-14.

The volume which yields approximately 6500–7000 CPM of specific binding and yields a IC50 value for cold SRIF of 60 pM–500 pM will be diluted with binding buffer so that 50 ul=6500–7000 CPM, and aliquoted appropriately (1 tube per 96 well plate) and frozen at –70° C.

Preparation of Test Compounds and Somatostatin-14

Non-radioactive somatostatin-14 (in the 14 amino acid residue form) is purchased from Sigma (Sigma #S-1763). The 1 mg lyophilized SRIF-14 is resuspended in 500 ul of DMSO, and then diluted with binding buffer to 122 ml to yield a concentration of 5 uM cold SRIF-14. 1 ml aliquots are stored frozen at –20° C. On the day of an experiment, the aliquot is thawed and serial diluted with binding buffer to the following concentrations:

| | Dilution Table (for SRIF-14) | | | |
|---|---|---|---|---|
| onc# | conc (nM) | Conc. wanted (nM) | dilution | Vol of st sol (ul) | vol buf (ul) |
| | 5000 | 20 | 250 | 5 | 1245 |
| | 20 | 10 | 2 | 500 | 500 |
| | 10 | 5 | 2 | 100 | 100 |
| | 5 | 2.5 | 2 | 100 | 100 |
| | 2.5 | 1.25 | 2 | 100 | 100 |
| | 1.25 | 0.625 | 2 | 100 | 100 |
| | 0.625 | 0.125 | 5 | 50 | 200 |
| | 0.125 | 0.025 | 5 | 50 | 200 |

10 nM, 5 nM, 2.5 nM, 1.25 nM, 0.625 nM, 0.125 nM, and 0.025 nM are used to add to various wells in triplicate as described later.

Various compounds are resuspended in 100% DMSO to yield a concentration of 5 mM. They are then diluted with binding buffer as follows:

Dilution Table (for compounds)

| onc# | conc (uM) | conc wanted (uM) | dilution | Vol of st sol (ul) | vol buff (ul) |
|---|---|---|---|---|---|
| | 5000 | 80 | 62.5 | 20.35 | 1251.525 |
| | 80 | 40 | 2 | 100 | 100 |
| | 40 | 20 | 2 | 100 | 100 |
| | 20 | 10 | 2 | 100 | 100 |
| | 10 | 5 | 2 | 100 | 100 |
| | 5 | 1 | 5 | 50 | 200 |
| | 1 | 0.2 | 5 | 50 | 200 |

80 uM, 40 uM, 20 uM, 10 uM, 5 uM, 1 uM, 0.2 uM are used to add to various wells in later.

96 well $bSST_2$ Membrane Binding Assay 100 ul of binding buffer is pipetted into each well of a 96 well block. 50 ul of compound stock is then added in triplicate to the appropriate wells.

All compound are tested in triplicate in the following format:

| | Compound 1 | Compound 2 | Compound 3 | Compound 4 |
|---|---|---|---|---|
| A | 1,2,3 | 4,5,6 | 7,8,9 | 10,11,12 |
| B | 1,2,3 | 4,5,6 | 7,8,9 | 10,11,12 |
| C | 1,2,3 | 4,5,6 | 7,8,9 | 10,11,12 |
| D | 1,2,3 | 4,5,6 | 7,8,9 | 10,11,12 |
| E | 1,2,3 | 4,5,6 | 7,8,9 | 10,11,12 |
| F | 1,2,3 | 4,5,6 | 7,8,9 | 10,11,12 |
| G | 1,2,3 | 4,5,6 | 7,8,9 | 10,11,12 |

Plate 2 will have compounds 5,6,7 & 8, and so on.

A cold somatostatin titration is always run as compound 1 on plate 1, and the concentrations of cold SRIF-14 are as follows:

```
A 1,2,3 = 1.667 nM final conc. (added conc is 10 nM)
B 1,2,3 = 0.833 nM
C 1,2,3 = 0.416 nM
D 1,2,3 = 0.208 nM
E 1,2,3 = 0.104 nM
F 1,2,3 = 0.0208 nM
G 1,2,3 = 0.0042 nM
```

All other compounds are tested with the following compound concentrations:

```
A n,n,n = 13,333 nM final conc. (added conc is 80 uM . . . )
B n,n,n = 6,666 nM
C n,n,n = 3,333 nM
D n,n,n = 1,666 nM
E n,n,n = 833.3 nM
F n,n,n = 166.6 nM
G n,n,n = 33 nM
```

The controls are set up in quadruplicate on each plate, in Row H. H 1,2,3,4 always provides total CPM pipetted into wells. H5,6,7,8 provides total membrane binding (no cold SRIF-14 added). H9,10,11,12 provides non-specific binding (50 ul of 5 uM cold SRIF is added to each well).

Next, 50 ul of $bSST_2$ membrane solution is added to each well, except to H1,2,3,4 on all plates. 100 ul of radiolabled $^{125}I$ somatostatin tracer solution is added to all wells except H1,2,3,4 on all plates.

The 96 well blocks are then sealed with plate seal tape, vortexed and placed on a titer plate shaker (Lab line instruments inc.), on setting 3, in the incubater at 37° C. The binding reaction is allowed to proceed for 1 hour. The plates are then taken off the shaker, vortexed, and the plate seal tape is removed (and placed in $^{125}I$ waste). A 250 ul volume from each well in the 96 well block is then transferred to its complementary well on the 96 well filter plate. Each plate is labeled appropriately to identify the compound # tested. Using a millipore vacuum apparatus, the filter plate is then bottom suctioned so that all liquid flows through the filter. 250 ul of wash buffer is then added to each well, and vacuum is applied to the plate to completely empty each well by vacuum filtration. The bottom of the plate is then blotted on napkins to remove any residual liquid. The, pipette 100 ul of radiolabeled SRIF-14 into wells: H1,2,3,4 on all plates (these are total CPM wells). To these same wells add 200 ul of Wallac 'Supermix' scintillation fluid. To all other wells, add 250 ul of Wallac 'Supermix' scintillation fluid. Seal both the bottom and top of plate with plate seal tape and place in Wallac cassette (1450-105). Read each plate using Wallac program ($SST_2$ filtermate). The raw CPM is downloaded into the Datafast program for evaluation, % bound is calculated for each compound concentration, and appropriate IC50's for each compound are thus generated. Note: % bound=(CPM-CPM(non-spec binding))/total mem-binding CPM×100. Each compound and it's IC50 is then reported into a database for SAR analysis.

Example 8

Rat Pituitary Assay for Somatostatin Receptor Antagonists

This assay is designed to quantitate the activity of antagonists of somatostatin that interact directly at the somatostatin receptor. The assay facilitates discovery of agents which increase growth hormone secretion by modulating the inhibitory effects of somatostatin. As aforementioned, somatostatin (also abbreviated SRIF) inhibits GH secretion in the anterior pituitary by binding to a high affinity membrane-bound (and G-protein coupled) receptor which is coupled negatively to adenyl cyclase, thereby reducing intracellular levels of cAMP that would otherwise facilitate, for example, secretion/release of GH from cytoplasmic granules. Vasoactive intestinal peptide (VIP) is one of several endogenous peptides that stimulates GH secretion by binding to a high affinity membrane-bound receptor coupled to a G protein-dependent signal transduction pathway. VIP activates adenylate cyclase and produces increased intracellular cAMP levels. These peptides may be involved in the coordinate regulation of GH secretion under physiologic conditions and be mediated through cAMP. The cell line used in the screen is a clonal pituitary cell that synthesizes and secretes GH in response to VIP and SRIF, and many other regulatory hormones, as expected for normal pituitary cells. The screen is designed to quantitate the ability of test agents to reverse SRIF's inhibition of the elevated intracellular cAMP levels produced by VIP. Note: in this procedure, the minimum sample size is about 1 mg.

In particular, cyclic AMP (cAMP) content of the pituitary cell line $GH_4C_1$ was used to differentiate somatostatin agonists from antagonists. The method was similar to that described by L. J. Dorflinger et al. ("Somatostatin inhibits vasoactive intestinal peptide-stimulated cyclic adenosine monophosphate accumulation in GH pituitary cells", *Endocrinology*, 113, pp. 1541–50, 1983) with the following modifications. Aliquots (50 μl) of $GH_4C_1$ cell suspension at 1–2 million cells/ml were added to 50 μl of each solution of test compound in Adenylyl Cyclase Activation FlashPlate® Assay plates from NEN™ Life Science Products (catalog SMP004A). Putative somatostatin agonists or antagonists were typically tested at concentrations of 10, 1 and 0.1 μM, in the presence of 100 nM vasoactive intestinal peptide (VIP; Sigma V3628) and 10 nM somatostatin 14 (cell culture tested, Sigma S1763). The FlashPlates®, which are coated with antibody against cAMP and contain scintillant integral to the plastic, are supplied as part of a kit with all necessary reagents to estimate cAMP content of whole cell preparations, including Stimulation Buffer, Detection Buffer, cAMP Standard, and [$^{125}$I]-cAMP Tracer. This afforded a convenient way to conduct a homogenous immunoradiometric assay of cAMP content in cells lysed in situ, following incubation of the cells with test compound. cAMP content in the $GH_4C_1$ cells was determined according to the manufacturer's instructions, by comparison with standards at concentrations from 10 to 1,000 nM cAMP. In this assay, VIP increased cAMP content of the $GH_4C_1$ cells, and somatostatin caused a partial inhibition. Test compounds acting as somatostatin antagonists were detected by their tendancy to increase cAMP content in comparison to control wells containing VIP and somatostatin but no test compound. Somatostatin agonists conversely decreased cAMP content. Accordingly, a detailed description of a preferred protocol is as follows.

Materials and Methods (a) Dulbecco's phosphate buffered saline (GibcoBRL #14040-141;PBS) containing 0.1% (w/v) BSA (Boehringer Mannheim #100-351), pH 7.4;

(b) F-10 nutrient media (GibcoBRL #11550-043) containing 2.5% fetal bovine serum (heat inactivated; Gemini Bio Products #100-107), horse serum (heat inactivated; GibcoBRL #26050-088) penicillin, and streptomycin (100 units/ml;100 ug/ml;GibcoBRL #15140-122);

(c) Cell Dissociation Solution (Sigma #C5789); and (d) Adenyl Cyclase Activation Flashplate Assay(NEN #SMP004A), with companion kit contains all the necessary reagents to estimate levels of cAMP in whole cell preparations, after stimulation of adenylate cyclase:
 A. Stimulation buffer
 B. Detection buffer
 C. cAMP standard
 D. FlashPlate
 E. [$^{125}$I]-cAMP tracer Peptides:

Somatostatin 14, cell culture tested (Sigma #S1763)
 Prepare 1 mM solution in deionized water
 Store aliquots at –20 C.

Vasoactive intestinal peptide (VIP; Sigma #V3628)
 Prepare 200 μM stock solution in PBS/BSA (store at –20 C.).
 Prepare 200 nM working solution in PBS/BSA.

Compound Diluent(optimized to test for receptor antagonists):
 Prepare 20 nM SRIF and 200 nM VIP in PBS/BSA cAMP standard
 Reconstitute the cAMP standard with 2 ml of deionized water (5 nmoles/ml;250 pmole/50 ul; store at 4 C. for <3 weeks); then prepare 1000, 500, 250, 100, 50, 25 and 10 pmole/ml solutions by appropriately diluting the stock solution with stimulation buffer.

Detection Mixture

Add 2 uCi (on calibration date) of cAMP-[$^{125}$I] tracer to 11 ml of Detection buffer for each flashplate. If the tracer is used after the calibration date, adjust the volume of tracer added to account for radioactive decay.

Equipment

Titer plate shaker; Lab Line Instruments
Microplate scintillation counter; Wallac microbeta,model 1450

Procedures (A) Cell preparation

Adherent GH4C1 cells are grown to about 75% confluence in 175 ml flasks. Cells are washed with PBS and harvested using 2.5 ml of Cell Dissociation Solution (listed above). Cells are resuspended in stimulation buffer and the number of cells is determined by manual counting using a hemocytometer. The cell concentration is adjusted to 1–2 million cells per ml by diluting the cell suspension with Stimulation Buffer (listed above).

(B) Preparation of test compounds

Compounds are dissolved in an appropriate volume of 100% DMSO to prepare a stock concentration of 10 mM (store solution at 4° C.). Typically, compounds are first evaluated at 10, 1, and 0.1 uM. To achieve these concentrations, 2× concentrations are prepared, i.e. 20, 2 & 0.2 uM in Compound Diluent.

(C) Assay procedure 1. cAMP standard curve:
Transfer 50 ul PBS/BSA to 16 consecutive wells of the flashplate. To these same wells, transfer 50 ul in duplicate of the 1000, 500, 250, 100, 50, 25, & 0 pmole/ml, and 5 nmole/ml cAMP solutions.

2. The following controls are included: transfer 50 ul in triplicate of PBS/BSA buffer to produce an unstimulated cAMP accumulation control; transfer 50 ul of 200 nM VIP to produce a maximally stimulated cAMP accumulation control, and transfer 50 ul of Compound diluent to produce a partial SRIF-inhibited cAMP accumulation control.

3. Transfer 50 ul of each test solution, in triplicate, to wells in the flashplate.

4. The assay is initiated by the addition of 50 ul of cell suspension to each well of the flashplate, except for wells containing the cAMP standards. The flashplate is covered and incubated at 37° C. for 20 minutes with mixing on a rotary platform (200 rpm).

5. Remove the flashplate from the incubator and add 100 ul of Detection buffer to all wells.

6. Place a plate cover on the flashplate and incubate for 16–24 hours at room temperature.

7. After incubation, count for $^{125}$I in the microplate scintillation counter.

Example 9

Effect of a Somatostatin Antagonist on GH Release in 12 kg Pigs

Studies indicate that concentrations of GH increase in small pigs within 10 minutes of administration of somatostatin antagonists, and then return to pre-treatment levels within 40 minutes post-administration.

The following protocol describes the effects of various doses of a somatostatin antagonist on release of endogenous porcine GH (or pST, porcine somatatrophin). Methods used to evaluate effects of compounds on plasma GH concentrations in barrows (castrated male pigs) were similar to those reported by M. J. Estienne et al., "Methyl-D,L-aspartate-induced growth hormone secretion in barrows: possible mechanisms of action", *Journal of Animal Science,*74, pp. 597–602, 1996, with the following modifications. Forty cross-bred barrows weighing approximately 12 kg were acclimatized for 2 days at 10 pigs per 36 sq. ft. pen, 4 pens per study, with feed (PS-9 swine starter diet) and water provided ad libitum. To enhance uniformity, two pigs/pen were eliminated based on being smallest or largest, or for health reasons, bringing the group size to 8 pigs/treatment. An equal number of pigs in each pen received 1 of 4 possible treatments at random, i.e. one of 3 doses of test compound or diluent alone. Compounds diluted in approximately 1 ml/pig sterile saline were administered by intramuscular injection into the rear leg (ham), about 1 minute after collection of the first blood sample into 7 ml heparinized evacuated tubes via jugular venepuncture. Blood samples were similarly collected at 10 minute intervals up to 40 minutes after injection of test compound or diluent. Plasma was separated by centrifugation and frozen at −20° C.).

Accordingly, a detailed description of a preferred protocol is as follows.

Experimental Animals a. Breed/strain: Crossbred pigs
b. Initial weight: Approximately 12 kg
c. Sex: Male castrate
d. Origin: Swinford/Frantz Farm, Hillsdale, Ind.
e. Identification: Eartag Management a. Feeding and watering method: ad libitum
b. Housing: thermostatically controlled heating
c. Diet: PS-9, swine starter diet
d. Pens: 10 pigs in each 36 sq. ft. pen.

Test Material

| Treatment | IM injection after time −1 bleed: | Pigs |
|---|---|---|
| T1 | Vehicle injected control | 5 |
| T2 | 2.5 mg/kg | 8 |
| T3 | 0.25 mg/kg | 8 |
| T4 | 0.025 mg/kg | 8 |

Procedure

Barrows were placed in pens for acclimation, eartagged, and a BW is recorded on day 1. General health observations will be recorded once daily. Two animals in each pen will be excluded. Criteria for exclusion include adverse health observations or the highest or lowest BW. Treatments are randomly assigned to pigs with the restriction that equal numbers of animals in each pen will receive each treatment.

The experimental compound is diluted with sterile saline to concentrations appropriate to achieve the target concentrations in the indicated animals, allowing also for a reasonable delivery volume. The volume injected (T2–T4) will vary to provide the appropriate dosage of test compound (for animals T2–T4) or diluent (for animal T1), and will be administered immediately after collection of a blood sample at time −1, with a 1 inch long-20 gauge needle attached to a 1 ml syringe. The volume of diluent for injection for T1 will be approximately 1 ml. The site of injection will be a rear leg (ham).

Blood samples are collected using 7 ml heparinized evacuated tubes at times −1, 10, 20, 30, and 40 min relative to the time of injection of test compound or diluent. Blood plasma is separated by centrifugation and frozen (−20° C.). Concentrations of pST are determined by competitive radio-immunoassay.

Observations/Measurements
1. Daily observation records;
2. Body weights on day −2 (minus 2)
3. Dosing records
4. Blood sample collection records, with detailed health observations at time of collection, and laboratory assay results.

Schedule of Activities

| DAY | TIME | Min | ACTIVITY |
|---|---|---|---|
| (−)2 | | | Animals arrived, eartagged, BW recorded. |
| 0 | | −1 | Collect blood sample, admin. compound, or diluent im, (back leg). |
| 0 | | 10 | Collect blood sample. |
| 0 | | 20 | Collect blood sample. |
| 0 | | 30 | Collect blood sample. |
| 0 | | 40 | Collect blood sample. |

Example 10

RIA Procedure for Determination of GH Levels in Plasma

The present assay is used to determine GH levels (for example, porcine GH or canine GH) in plasma samples.

The double antibody radioimmunoassay (RIA) used to determine porcine GH concentrations in plasma samples was similar to that described by Y. N. Sinha et al., "Studies of GH secretion in mice by a homologous radioimmunoassay for mouse GH", *Endocrinology,*91, pp.784–92, 1972, and those) and that of F. Cocola et al., "A rapid radioimmunoassay method of growth hormone in dog plasma", *Proceedings of the Society for Experimental Biology and Medicine,*151, pp. 140–14, 1976. Modifications were as follows. Native porcine GH (pGH) for radioiodination as tracer, canine GH for use as standard (cGH; AFP-1983B; the aminoacid sequence of canine and porcine GH are the same), and primary antibody (monkey anti-cGH; AFP-21452) were supplied by A. F. Parlow, Harbor UCLA Medical Center. Recombinant porcine GH from Biogenesis was alternatively used for radioiodination as tracer. Radio-iodinations were conducted by Biomedical Technologies Inc, Stoughton, Mass. Primary antibody (1:50,000 or 1:100,000 final dilution), normal monkey serum (ICN 55988; 1:1,000 final dilution), and plasma sample or standard (0.08 to 2.5 ng cGH/tube) were mixed and incubated for 2 hours at ambient temperature, then tracer (10,000 cpm/tube) was added and the incubation continued for a further 20 hours at ambient temperature in a total volume of 500 µl. Secondary antibody (goat anti-monkey IgG ICN 55418; final dilution 1:160) and polyethyleneglycol 8,000 (final concentration 44 mg/ml) were added and mixed in a final volume of 1.6 ml. Tubes were incubated at 4° C. for 2 hours with shaking, then they were centrifuged, supernates discarded, and the gamma-emission of the pellets determined.

Accordingly, a detailed description of a preferred protocol is as follows.

Materials

Sodium Phosphate, monobasic

Sodium Phosphate, dibasic

DI water

Tetrasodium ethylene diamine tetracetic acid (EDTA Na4)

Bovine serum albumin (BSA)

Sodium chloride (NaCl)

Normal Monkey Serum (NMS): ICN #55988 1 vial=2 ml serum

Polyethylene Glycol (MW 8,000) (PEG): Sigma #P2263

Antiserum to canine growth hormone (Monkey) (1° Ab), courtesy Dr. A. F. Parlow, Harbor UCLA Med Center, #AFP-21452

Goat Anti-monkey IgG (2° Ab); ICN #55418 pGH for iodination: Dr. A. F. Parlow or Biogenesis (iodination has been done by Ron Forand at BTI)

cGH for iodination: Dr. A F Parlow (iodination by Ron Forand, BTI) GH reference standard: Dr. A F Parlow #AFP-1983B Solution Preparation 1) 0.5 M Sodium phosphate, pH 7.4:

make 1 liter of 0.5M monobasic solution: 68.99 g monobasic in 1 liter water make 1 liter of 0.5M dibasic solution: 70.98 g dibasic in 1 liter water add the monobasic to the dibasic solution until the pH is 7.4.

Store at RT 2) 0.5M EDTA, pH 7.5

Dissolve 113 g of EDTA, Na4 in 500 mls DI water. Stir to dissolve.

Adjust pH to 7.5 with acetic acid. Refrigerate.

3) RIA Buffer: 0.5% BSA; 0.1M Sodium phosphate, pH 7.4; 0.1M NaCl; 25 mM

EDTA,Na4; pH 7.5

In a 1 liter flask:

5 g BSA 200 ml 0.5M Sodium phosphate, pH 7.4

5.84 g NaCl 50 mL 0.5 M EDTA

Bring to 1 liter with DI water, store at RT

4) NMS (0.5%)

To one vial NMS add 2 ml RIA buffer. Dilute the NMS solution to a 0.5% final concentration by adding an additional 398 ml RIA buffer. Store in 40 ml aliquots at −70° C.

5) 7% PEG (MW: 8,000)

Dissolve 70 g PEG in 1000 ml of 0.05M sodium phosphate, pH 7.4 (100 ml of 0.5M Sodium phosphate+ 900 ml water)

6) 1° Antibody (1:100) Stock #1: To the original vial add 0.8 ml DI water. Freeze in 50 ul aliquots at −70° C.

(1:500) Stock #2: Dilute one tube of Stock #1, 1:5 (add 200 ul) with RIA buffer.

Final dilution of Stock #2 1° Ab is determined with every new lot of 1° Ab based on percent binding (usually an additional 1:100 to 1:200 dilution of Stock #2)

7) 2° Antibody

Bring contents of 1 vial up in 2 ml RIA buffer. Dilute 1:10 (20 ml total volume) with RIA buffer. Store at −70° after reconstitution RIA Procedure Day 1

1. Label tubes (standards in triplicate; samples in duplicate)

1–4 for Total counts

5–9 for Non-specific binding

10–12 for Blanks

13–15 Standard 1 (0.08 ng/tube)

16–18 Standard 2 (0.16 ng/tube)

19–21 Standard 3 (0.32 ng/tube)

22–24 Standard 4 (0.64 ng/tube)

25–27 Standard 5 (1.25 ng/tube)

28–30 Standard 6 (2.5 ng/tube)

31 and higher, Samples in duplicate and control plasma (pooled plasma from Lampire)

Note: Calculated concentrations for samples are initially reported as ng/tube. Values are multiplied by 10 for ng/ml concentrations and reported in this format (based on a 100 ul sample volume per tube.)

2. Standard Preparation

A. Dissolve 1 vial (5 ug) cGH standard (Parlow) in 1 ml water

B. Store in 200 ul aliquots at −70° C.

C. Take one 200 ul aliquot and break into 20 ul aliquots (−70° C.)

Use one 20 ul aliquot for standard prep.

Std 6: 10 ul cGH std (5 ug/ml) in 990 ul RIA buffer

Std 5: 500 ul Std 6+500 ul RIA buffer

Std 4: 500 ul Std 5+500 ul RIA buffer

Std 3: 500 ul Std 4+500 ul RIA buffer

Std 2: 500 ul Std 3+500 ul RIA buffer

Std 1: 500 ul Std 2+500 ul RIA buffer

3. Thaw NMS, 1° Ab and samples.

4. Add RIA buffer in the following amounts:

Tubes 5–12: 300 ul

Tubes 13–30: 250 ul

Tubes 31–?: 200 ul

5. Add 50 ul of standard solution to the corresponding tubes.

Add 100 ul of sample to the corresponding tubes.

6. Add 100 ul NMS to tubes 5–9

7. Vortex the tubes

8. Add 100 ul of 1° canine antibody (final dilution of Stock #2) to tubes 10 and up (Dilution is made with NMS).

9. Shake the tubes at RT for 2 hrs.

10. Tracer preparation:

A 1:50 dilution of the starting tracer is made. The 1:50 dilution is titrated for every new lot of tracer to determine how many ul of 1:50 solution provides ~10,000 cpm. This number of ul of 1:50 is then used per tube.

Working solution is prepared by bringing the selected 1:50 volume per tube to 100 ul total (per tube ) with RIA buffer.

i.e. 1:50—64 ul start tracer+3136 ul RIA buffer, mix working solution—3120 ul 1:50 solution+48880 ul RIA buffer, mix 11. Add 100 ul of working solution to all the tubes porcine tracer is used for swine samples canine tracer is used for dog samples 12. Vortex the tubes 13. Shake the tubes at RT for 20 hrs.

Day 2

14. Add 100 ul 2° Ab to tubes 5 and higher

15. Add 1 ml PEG solution to tubes 5 and higher
16. Vortex the tubes
17. Shake the tubes at 4° C. for 2 hrs
18. Remove tubes 1–4 and centrifuge remaining tubes at 3000 rpm, 4° C., for 30 min.
19. Discard the supernatants. Invert the tubes in a paper towel lined tub for 5–10 minutes to drain.
20. Replace tubes 1–4
21. Count for 3 min, curve is done by log-logit, values are in ng/tube and are then multiplied by ten for ng/ml concentration.

What is claimed is:

1. A compound according to the formula

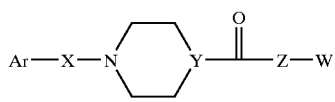

or a pharmaceutically acceptable salt, solvate or hydrate thereof; wherein

Ar is a $(C_6-C_{10})$aryl or $(C_1-C_9)$heteroaryl group that is optionally substituted;

X is a direct link, —CH$_2$—, —SO$_2$—, —CO—, —CHR$^1$— where R$^1$ is $(C_1-C_6)$alkyl, or —CR$^{1'}$R$^{1''}$— where both R$^{1'}$ and R$^{1''}$ are, independently, $(C_1-C_6)$ alkyl;

Y is N or CH;

Z is selected from the groups consisting of:

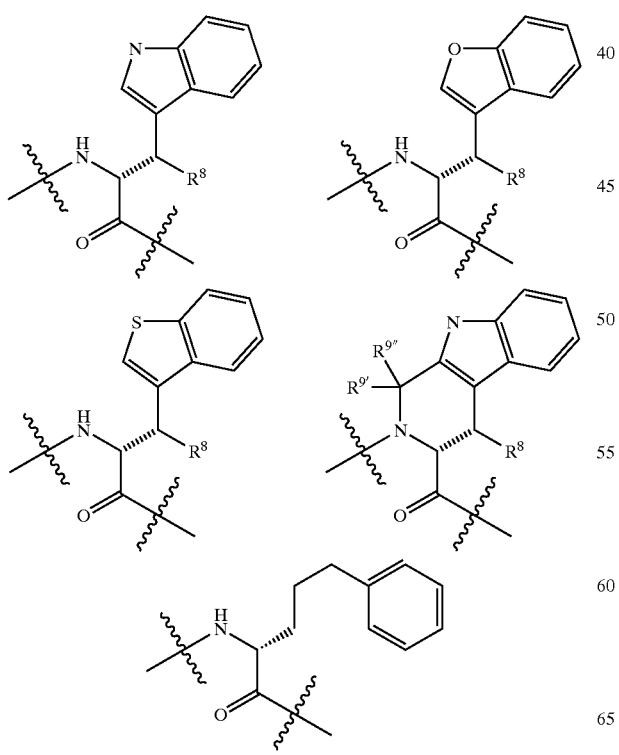

wherein R$^8$, if present, is H, or $(C_1-C_6)$ alkyl;

R$^{9'}$ and R$^{9''}$, if present, are each independently selected from the group consisting of H, $(C_1-C_6)$alkyl, $(C_1-C_9)$heteroaryl$(C_1-C_6)$alkyl, and $(C_6-C_{10})$aryl $(C_1-C_6)$alkyl;

W is selected from (a) and (b):

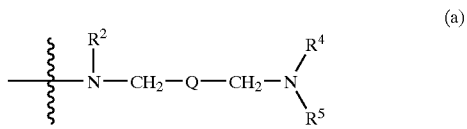

(a)

wherein

R$^2$, R$^4$ and R$^5$ are each independently selected from: H; $(C_1-C_6)$ alkyl, optionally substituted with one or more halo or trifluoromethyl groups; and benzyl, optionally substituted with one or more halo or trifluoromethyl groups; and Q is selected from
(i) $(C_6-C_{10})$ aryl;
(ii) $(C_1-C_9)$ heteroaryl;
(iii) $(C_3-C_{10})$cycloalkyl; and
(iv) $(C_3-C_{10})$heterocycloalkyl;

wherein each of said groups (i) to (iv) is optionally substituted with one or more groups that are independently selected from halo, $(C_1-C_6)$ alkoxy, and $(C_1-C_6)$ alkyl; and

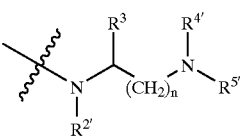

(b)

wherein

R$^{2'}$, R$^{4'}$ and R$^{5'}$ are each independently selected from the group consisting of H; $(C_1-C_6)$ alkyl, optionally substituted by one or more halo or trifluoromethyl groups; and benzyl, also optionally substituted by one or more halo or trifluoromethyl groups;

n is 2 to 5; and

R$^3$ is selected from the groups consisting of
(i) H; $(C_1-C_6)$alkyl, optionally substituted by one or more halo or trifluoromethyl groups; and benzyl, also optionally substituted by one or more halon or trifluoromethyl groups;

(ii)

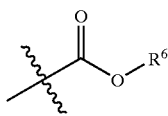

where R[6] is H; (C$_1$–C$_6$)alkyl, optionally substituted by one or more halo or trifluoromethyl groups; or benzyl, optionally substituted by one or more halo or trifluoromethyl groups; and (iii)

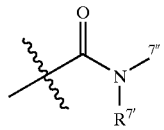

where R[7'] and R[7''] are each, independently, H; (C$_1$–C$_6$)alkyl, optionally substituted by one or more halo or trifluoromethyl groups; or benzyl, optionally substituted by one or more halo or trifluoromethyl groups.

2. The compound of claim 1, wherein group Ar is a (C$_6$–C$_{10}$) aryl group selected from phenyl and naphthyl.

3. The compound of claim 1, wherein group Ar is a a (C$_1$–C$_9$) heteroaryl group that is selected from the group consisting of furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, and benzoxazinyl.

4. The compound of claim 1, wherein group Ar is optionally substituted by one to five groups, each independently selected from the group consisting of hydroxy, halo, amino, trifluoromethyl, carboxy, (C$_1$–C$_6$)alkoxy-, (C$_1$–C$_6$)acyloxy-, (C$_1$–C$_6$)alkylamino-, ((C$_1$–C$_6$)alkyl)$_2$amino-, (C$_1$–C$_6$)acylamino-, cyano, nitro, (C$_1$–C$_6$)alkyl-, (C$_2$–C$_6$)alkenyl-, (C$_2$–C$_6$)alkynyl-, (C$_1$–C$_6$)acylamino-, cyano(C$_1$–C$_6$)alkyl-, trifluoromethyl(C$_1$–C$_6$)alkyl-, nitro(C$_1$–C$_6$)alkyl-, (C$_1$–C$_3$)alkyl(difluoromethylene)(C$_1$C$_3$)alkyl-, (C$_1$–C$_6$)acylamino (C$_1$–C$_6$)alkyl-, (C$_1$–C$_6$)alkoxy(C$_1$–C$_6$)acylamino-, amino (C$_1$–C$_6$)acyl-, amino(C$_1$C$_6$)acyl(C$_1$–C$_6$)alkyl-, (C$_1$–C$_6$) alkylamino(C$_1$–C$_6$)acyl-, ((C$_1$–C$_6$)alkyl)$_2$amino(C$_1$–C$_6$) acyl-, (C$_3$–C$_{10}$)cycloalkyl(C$_1$–C$_6$)alkyl-, (C$_1$–C$_6$)acyloxy (C$_{1-C6}$)alkyl-, (C$_2$–C$_6$)alkoxy(C$_1$–C$_6$)alkyl-, piperazinyl (C$_1$–C$_6$)alkyl-, (C$_1$–C$_6$)acylamino(C$_1$–C$_6$)alkyl-, (C$_6$–C$_{10}$) aryl(C$_1$–C$_6$)alkoxy(C$_1$–C$_6$)alkyl-, (C$_2$–C$_9$)heteroaryl (C$_1$–C$_6$)alkoxy(C$_1$–C$_6$)alkyl-, (C$_1$–C$_6$)alkylthio(C$_1$–C$_6$) alkyl-, (C$_6$–C$_{10}$)arylthio(C$_1$–C$_6$)alkyl-, (C$_1$–C$_6$)alkylsulfinyl (C$_1$–C$_6$)alkyl- (C$_6$–C$_{10}$)arylsulfinyl(C$_1$–C$_6$)alkyl-, (C$_1$–C$_6$) alkylsulfonyl(C$_1$–C$_6$)alkyl-, (C$_6$–C$_{10}$)arylsulfonyl(C$_1$–C$_6$) alkyl-, amino(C$_1$–C$_6$)alkyl-, (C$_1$–C$_6$)alkylamino(C$_1$–C$_6$) alkyl-, (C$_1$–C$_6$)alkyl(difluoromethylene)-, (C$_1$–C$_3$)alkyl (difluoromethylene)(C$_1$–C$_3$)alkyl-, (C$_1$–C$_6$)alkoxy(C$_1$–C$_6$) acyl-, (C$_1$–C$_6$)alkylamino(C$_1$–C$_6$)acyl-, ((C$_1$–C$_6$)alkyl)$_2$ amino(C$_1$–C$_6$)acyl-, (C$_6$–C$_{10}$)aryl-, (C$_5$–C$_9$)heteroaryl-, (C$_6$–C$_{10}$)aryl(C$_1$–C$_6$)alkyl-, (C$_2$–C$_9$)heteroaryl(C$_1$–C$_6$) alkyl-, (C$_6$–C$_{10}$)aryl(C$_6$–C$_{10}$)aryl-, (C$_6$–C$_{10}$)aryl(C$_6$–C$_{10}$) aryl(C$_1$–C$_6$)alkyl- (C$_3$–C$_{10}$)cycloalkyl-, (C$_3$–C$_6$)cycloalkyl (C$_1$–C$_6$)alkyl-, (C$_3$–C$_{10}$)heterocycloalkyl-, (C$_3$–C$_{10}$) heterocycloalkyl(C$_1$–C$_6$)alkyl-, hydroxy(C$_2$–C$_6$)alkyl-, (C$_1$–C$_6$)acyloxy(C$_2$–C$_6$)alkyl-, (C$_1$–C$_6$)alkoxy(C$_2$–C$_6$) alkyl-, piperazinyl(C$_1$–C$_6$)alkyl-, (C$_1$–C$_6$)acylamino (C$_1$–C$_6$)alkyl-, (C$_6$–C$_{10}$)aryl(C$_1$–C$_6$)alkoxy(C$_1$–C$_6$)alkyl-, (C$_2$–C$_9$)heteroaryl(C$_1$–C$_6$)alkoxy(C$_1$–C$_6$)alkyl-, (C$_1$–C$_6$) alkylthio(C$_1$–C$_6$)alkyl-, (C$_6$–C$_{10}$)arylthio(C$_1$–C$_6$)alkyl-, (C$_1$–C$_6$)alkylsulfinyl(C$_1$–C$_6$)alkyl-, (C$_6$–C$_{10}$)arylsulfinyl (C$_1$–C$_6$)alkyl-, (C$_1$–C$_6$)alkylsulfonyl(C$_1$–C$_6$)alkyl-, (C$_6$–C$_{10}$)arylsulfonyl(C$_1$–C$_6$)alkyl-, amino(C$_1$–C$_6$)alkyl-, (C$_1$–C$_6$)alkylamino(C$_1$–C$_6$)alkyl-, and ((C$_1$–C$_6$)alkyl)$_2$ amino(C$_1$–C$_6$)alkyl.

5. The compound of claim 1, wherein group Q of group W, option (a), is a (C$_6$–C$_{10}$) aryl group selected from phenyl and naphthyl.

6. The compound of claim 1, wherein group Q of group W, option (a), is a (C$_1$–C$_9$) heteroaryl group that is selected from the group consisting of furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, and benzoxazinyl.

7. The compound of claim 1, wherein group Q of group W, option (a), is a (C$_3$–C$_{10}$)cycloalkyl group that is selected from the group consisting of cyclopropyl, cyclobutyl, cyclopentyl, cyclohexyl, cycloheptyl, cyclopropenyl, cyclobutenyl, cyclopentenyl, cyclohexenyl, cycloheptenyl, 1,3-cyclobutadienyl, 1,3-cyclopentadienyl, 1,3-cyclohexadienyl, 1,4-cyclohexadienyl, 1,3-cycloheptadienyl, 1,4-cycloheptadienyl, 1,3,5-cycloheptatrienyl, bicyclo[3.2.1]octane, bicyclo[2.2.1] heptane, and the norborn-2-ene unsaturated form thereof.

8. The compound of claim 1, wherein group Q of group W, option (a), is a (C$_3$–C$_{10}$)heterocycloalkyl group that is selected from the group consisting of pyrrolidinyl, tetrahydrofuranyl, dihydrofuranyl, tetrahydropyranyl, pyranyl, thiopyranyl, aziridinyl, oxiranyl, methylenedioxyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, tetrahydroazepinyl, piperazinyl, and chromanyl.

9. The compound of claim 1, selected from the group consisting of:

6-Amino-2-[2-[(1-benzenesulfonyl-piperidine-4-carbonyl)-amino]-3-(1H-indol-3-yl)-propionylamino]-hexanoic acid tert-butyl ester;

6-Amino-2-[2-[(4-benzoyl-piperazine-1-carbonyl)-amino]-3-(1H-indol-3-yl)-propionylamino]-hexanoic acid tert-butyl ester;

6-Amino-2-(3-(1H-indol-3-yl)-2-{[4-(4-methyl-benzoyl)-piperazine-1-carbonyl]-amino}-propionylamino)-hexanoic acid tert-butyl ester;

6-Amino-2-[2-[(4-benzenesulfonyl-piperazine-1-carbonyl)-amino]-3-(1H-indol-3-yl)-propionylamino]-hexanoic acid tert-butyl ester; and 6-Amino-2(3-(1H-indol-3-yl)-2-{[4-(toluene-4-sulfonyl)-piperazine-1-carbonyl]-amino}-propionylamino)-hexanoic acid tert-butyl ester.

10. The compound of claim 1, selected from the group consisting of:

4-(Toluene-4-sulfonyl)-piperazine-1-carboxylic acid[1-[(4-aminomethyl-pyridin-2-ylmethyl)-carbamoyl]-2-(1H-indol-3-yl)-ethyl]-amide;

6-Amino-2-(3-(1H-indol-3-yl)-2-{[4-(toluene-4-sulfonyl)-piperazine-1-carbonyl]-amino}-butyrylamino)-hexanoic acid tert-butyl ester;

6-Amino-2-[2-{[4-(4-fluoro-benzenesulfonyl)-piperazine-1-carbonyl]-amino}-3-(1H-indol-3yl)-propionylamino]-hexanoic acid tert-butyl ester;

4-Benzenesulfonyl-piperazine-1-carboxylic acid[1-[(4-aminomethyl-pyridin-2-ylmethyl)-carbamoyl]-2-(1H-indol-3-yl)-ethyl]-amide;

6-Amino-2-[2-[(4-benzenesulfonyl-piperazine-1-carbonyl)-amino]-3-(1H-indol-3-yl)-butyrylamino]-hexanoic acid tert-butyl ester;

6-Amino-2-[2-{[4-(4-chloro-benzenesulfonyl)-piperazine-1-carbonyl]-amino}-3-(1H-indol-3-yl)-propionylamino]-hexanoic acid tert-butyl ester;

4-(4-Methyl-benzoyl)-piperazine-1-carboxylic acid[1-[(4-aminomethyl-pyridin-2-ylmethyl)-carbamoyl]-2-(1H-indol-3-yl)-ethyl]-amide;

6-Amino-2-(3-(1H-indol-3-yl)-2-{[4-(4-methyl-benzoyl)-piperazine-1-carbonyl]-amino}-butyrylamino)-hexanoic acid tert-butyl ester;

6-Amino-2-[2-{[4-(4-fluoro-benzoyl)-piperazine-1-carbonyl]-amino}-3-(1H-indol-3-yl)-propionylamino]-hexanoic acid tert-butyl ester;

4-Benzoyl-piperazine-1-carboxylic acid[1-[(4-aminomethyl-pyridin-2-ylmethyl)-carbamoyl]-2-(1H-indol-3-yl)-ethyl]-amide;

6-Amino-2-[2-[(4-benzoyl-piperazine-1-carbonyl)-amino]-3-(1H-indol-3-yl)-butyrylamino]-hexanoic acid tert-butyl ester;

6-Amino-2-[2-{[4-(4-chloro-benzoyl)-piperazine-1-carbonyl]-amino}-3-(1H-indol-3-yl)-propionylamino]-hexanoic acid tert-butyl ester;

1-(Toluene-4-sulfonyl)-piperidine-4-carboxylic acid[1-[(4-aminomethyl-pyridin-2-ylmethyl)-carbamoyl]-2-(1H-indol-3-yl)-ethyl]-amide;

6-Amino-2-(3-(1H-indol-3-yl)-2-{[1-(toluene-4-sulfonyl)-piperidine-4-carbonyl]-amino}-butyrylamino)-hexanoic acid tert-butyl ester;

6-Amino-2-[2-{[1-(4-fluoro-benzenesulfonyl)-piperidine-4-carbonyl]-amino}-3-(1H-indol-3-yl)-propionylamino]-hexanoic acid tert-butyl ester;

1-Benzenesulfonyl-piperidine-4-carboxylic acid[1-[(4-aminomethyl-pyridin-2-ylmethyl)-carbamoyl]-2-(1H-indol-3-yl)-ethyl]-amide;

6-Amino-2-[2-[(1-benzenesulfonyl-piperidine-4-carbonyl)-amino]-3-(1H-indol-3-yl)-butyrylamino]-hexanoic acid tert-butyl ester;

6-Amino-2-[2-{[1-(4-chloro-benzenesulfonyl)-piperidine-4-carbonyl]-amino}-3-(1H-indol-3-yl)-propionylamino]-hexanoic acid tert-butyl ester;

1-(4-Methyl-benzoyl)-piperidine-4-carboxylic acid[1-[(4-aminomethyl-pyridin-2-ylmethyl)-carbamoyl]-2-(1H-indol-3-yl)-ethyl]-amide;

6-Amino-2-(3-(1H-indol-3-yl)-2-{[1-(4-methyl-benzoyl)-piperidine-4-carbonyl]-amino}-butyrylamino)-hexanoic acid tert-butyl ester;

6-Amino-2-[2-{[1-(4-fluoro-benzoyl)-piperidine-4-carbonyl]-amino}-3-(1H-indol-3-yl)-propionylamino]-hexanoic acid tert-butyl ester;

1-Benzoyl-piperidine-4-carboxylic acid[1-[(4-aminomethyl-pyridin-2-ylmethyl)-carbamoyl]-2-(1H-indol-3-yl)-ethyl]-amide;

6-Amino-2-[2-[(1-benzoyl-piperidine-4-carbonyl)-amino]-3-(1H-indol-3-yl)-butyrylamino]-hexanoic acid tert-butyl ester; and 6-Amino-2-[2-{[1-(4-chloro-benzoyl)-piperidine-4-carbonyl]-amino}-3-(1H-indol-3-yl)-propionylamino]-hexanoic acid tert-butyl ester.

11. A compound according to the formula

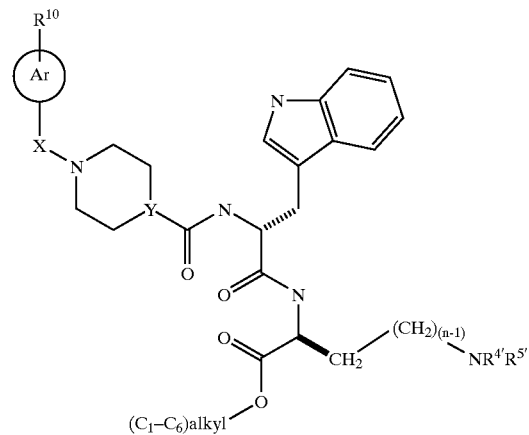

or a pharmaceutically acceptable salt, solvate, or hydrate thereof; wherein

Ar is a $(C_6-C_{10})$aryl or $(C_1-C_9)$heteroaryl group that is optionally substituted;

X is a direct link, —$CH_2$—, —$SO_2$—, —CO—, —$CHR^1$— where $R^1$ is $(C_1-C_6)$alkyl, or —$CR^{1'}R^{1''}$— where both $R^{1'}$ and $R^{1''}$ are, independently, $(C_1-C_6)$ alkyl;

Y is N or CH;

$R^{10}$ represents from 0 to 5 optional substituent groups, each independently selected from halo, cyano, carboxy, $(C_1-C_6)$alkyl, and $(C_1-C_6)$alkoxy;

$R^{4'}$ and $R^{5'}$ are each independently selected from H; $(C_1-C_8)$ alkyl, optionally substituted by one or more halo or trifluoromethyl groups; and benzyl, also optionally substituted by one or more halo or trifluoromethyl groups; and n is 1 to 4.

12. A compound according to claim 1 wherein $R^2$ or $R^{2'}$ is $(C_1-C_8)$alkyl- or benzyl-, optionally substituted by one or more halo or trifluoromethyl groups.

13. A compound according to claim 1 wherein one or more of $R^3$, $R^4$, $R^{4'}$, $R^5$, $R^{5'}$, and $R^6$ is $(C_1-C_8)$alkyl- or benzyl-, optionally substituted by one or more halo or trifluoromethyl groups.

14. A compound according to claim 1 wherein $R^7$ or $R^{7'}$ is $(C_1-C_8)$alkyl- or benzyl-, optionally substituted by one or more halo or trifluoromethyl groups.

15. A composition for promoting growth hormone secretion in a mammal, comprising an effective amount of a compound according to claim 1, and a pharmaceutically acceptable carrier.

16. A composition for inhibiting the binding of somatostatin to a somatostatin receptor type 2 (sst2), comprising an effective amount of a compound according to claim 1, and a pharmaceutically acceptable carrier.

17. A method for promoting growth hormone secretion in a mammal, comprising administering an effective amount of a composition according to claim 15.

18. A method for promoting secretion of gastrin or glucagon in a mammal, comprising administering an effective amount of a composition according to claim 15.

19. A method for inhibiting somatostatin-induced down-regulation of growth hormone secretion in a mammal, comprising administering an effective amount of a composition according to claim 16.

20. A method for promoting the sustained secretion of growth hormone in a mammal in need thereof, wherein said mammal possesses:
  (a) a defect in (1) the expression of the encoding nucleotide sequence for growth hormone, (2) the processing of resultant mRNA, or (3) the translation or intracellular processing and packaging of GH or precursor polypeptide thereof; or
  (b) an allele of the growth hormone gene which codes for a growth hormone polypeptide that is insufficiently active;
  which comprises administering an effective amount of a composition according to claim 15.

21. A composition for promoting growth hormone secretion in a mammal, comprising an effective amount of a compound according to claim 1, an optional pharmaceutically acceptable carrier and a growth hormone releasing peptide (GHRP) or a growth hormone releasing hormone (GHRH).

22. A method for promoting growth hormone secretion in a mammal, comprising administering an effective amount of a composition according to claim 21.

23. A method for promoting growth hormone secretion in a mammal, comprising administering an effective amount of a composition according to claim 15, and a further composition comprising growth hormone releasing peptide (GHRP) or growth hormone releasing hormone (GHRH).

* * * * *